(12) United States Patent
Pappin et al.

(10) Patent No.: US 7,868,547 B2
(45) Date of Patent: Jan. 11, 2011

(54) DETERMINATION OF ANALYTE CHARACTERISTICS BASED UPON BINDING PROPERTIES

(75) Inventors: Darryl J. Pappin, Boxborough, MA (US); Philip L. Ross, Westborough, MA (US); Steven R. Guertin, Lunenburg, MA (US)

(73) Assignee: DH Technologies Development Pte. Ltd., Singapore (SG)

( * ) Notice: Subject to any disclaimer, the term of this patent is extended or adjusted under 35 U.S.C. 154(b) by 186 days.

(21) Appl. No.: 11/069,277

(22) Filed: Mar. 1, 2005

(65) Prior Publication Data

US 2005/0208550 A1 Sep. 22, 2005

Related U.S. Application Data

(60) Provisional application No. 60/549,049, filed on Mar. 1, 2004.

(51) Int. Cl.
*H01J 17/26* (2006.01)
(52) U.S. Cl. ..................................... 313/564
(58) Field of Classification Search ........................ None
See application file for complete search history.

(56) References Cited

U.S. PATENT DOCUMENTS

| | | | |
|---|---|---|---|
| 5,705,610 A | 1/1998 | Zuckermann et al. | |
| 5,800,992 A | 9/1998 | Foder et al. | |
| 6,027,890 A | 2/2000 | Van Ness et al. | |
| 6,270,976 B1 | 8/2001 | Schmidt et al. | |
| 6,287,780 B1 | 9/2001 | Schmidt et al. | |
| 6,475,807 B1 | 11/2002 | Geysen et al. | |
| 7,195,751 B2 * | 3/2007 | Pappin et al. | 424/1.81 |
| 2003/0153007 A1 | 8/2003 | Chen et al. | |

FOREIGN PATENT DOCUMENTS

| | | |
|---|---|---|
| WO | WO 98/31830 A | 7/1998 |
| WO | WO 2004/019000 A | 3/2004 |
| WO | WO 2004/070352 A | 8/2004 |
| WO | WO 2005/068446 A | 7/2005 |

OTHER PUBLICATIONS

Berger et al. "High-throughput Global Peptide Proteomic Analysis by Combining Stable Isotope Amino Acid Labeling and Data-Dependent Multiplexed-MS/MS", Anal. Chem. 2002, 74:4994-5000.*
Thompson et al. "Tandem mass tags: a novel quantification strategy for comparative analysis of complex protein mixtures by MS/MS", Anal. Chem., 2003, 75:1895-1904.*
Bonenfant, Debora et al., "Quantitation of changes in protein phosphorylation: A simple method based on stable isotope labeling and mass spectrometry", Proceedings of the National Academy of Sciences of the United States of America, vol. 100, No. 3, Feb. 4, 2003, pp. 880-885.
Goshe, M.B. et al., "Phosphoprotein isotope-coded affinity tag approach for isolating and quantitating phosphopeptides in proteome-wide analyses", Analytical Chemistry, American Chemical Society, Columbus, US. vol. 73, No. 11, Jun. 1, 2001, pp. 2578-2586.
Sechi, S. et al., "Quantitative Proteomics Using Mass Spectrometry", Current Opinion in Chemical Biology, Current Biology Ltd., London, GB, vol. 7, No. 1, Feb. 2003, pp. 70-77.
Aebersold, R. et al., "Mass Spectrometry in Proteomics", Chemical Reviews, American Chemical Society, Easton, US, vol. 101, No. 2, Feb. 2001, pp. 269-295.
PCT/US2005/006457 International Search Report.
Press Release: Applied Biosystems Introduces a New Multiplexed Reagent for Protein and Biomarker Quantitation at American Society of Mass Spectrometry, May 20, 2004.
Applied Biosystems Application Note: iTRAQ™ Reagents, Multiplex Protein Quantitation in *Saccaromyces cerevisiae* using iTRAQ™ Reagents with the QSTAR® XL System and the 4700 Proteomics Discovery System, May 2004.
Applied Biosystems Product Bulletin: iTRAQ™ Reagents, Amine-specific Labeling Reagents for Multiplexed Relative and Absolute Protein Quantitation, May 2004.
Medzihradszky et al., "Peptide sequence determination by matrix-assisted laser desorption ionization [MALDI] employing a tandem double focusing magnetic-orthogonal acceleration time-of-flight mass spectrometer", *Journal of the American Chemical Society for Mass Spectrometry*, 7(1): 1-10 (1996).
Gill et al, "Resolution of Isobaric and Isomeric Ions Using Chemical Shifts in an Ion Trap Mass Spectrometer" *Analytical Chemistry*, 70(20): 4448-4458 (1998).
Glish et al, "Determination of daughter ion formulas by multiple stages of mass spectrometry", *Journal of the American Chemical Society for Mass Spectrometry*, 1(2): 166-173 (1990).
Duffield et al, "Mass spectrometry in structural and stereochemical problems. LVIII. Fragmentation processes of some lactams." *Journal of the American Chemical Society*, 86(24): 5536-5541 (1964).
Bottari P et al: "Design and Synthesis of Visible Isotope-Coded Affinity Tags for the Absolute Quantification of Specific proteins in Complex Mixtures" Bioconjugate Chemistry, ACS, Washington, D.C., U.S. vol. 15, No. 2, Feb. 21, 2004, pp. 380-388.
Dunayevskiy, Yuriy M.: "Application of Capillary Electrophoresis-Electrospray ionization Mass Spectrometry in the Determination of Molecular Diversity"; PNAS 1996, Proc. Natl. Acad. Sci. USA 93—Boston, MA, Jan. 30, 1996, pp. 6152-6157.
Gygi S P et al: "Quantitative Analysis of Complex Protein Mixtures using Isotope-Coded Affinity Tags" Nature Biotechnology, nature Publishing Group, New York, NY, U.S. vol. 17, No. 10, Oct. 1, 1999, pp. 994-999.
PCT/US2005/006457 International Search Report, May 9, 2005.

* cited by examiner

*Primary Examiner*—Jon P Weber
*Assistant Examiner*—Bin Shen
(74) *Attorney, Agent, or Firm*—Kilyk & Bowersox, P.L.L.C.

(57) ABSTRACT

Embodiments of the present invention relate to the determination of analyte characteristics based upon binding properties using mass analysis and differential labeling reagents.

26 Claims, 13 Drawing Sheets

Scheme A For The Synthesis Of Various Active Esters Of N-Methyl Piperazine
Via Imidazolide Formation Scheme B For The Synthesis Of Various Active Esters Of N-Methyl Piperazine Via Oxallyl Chloride Scheme C For The Synthesis Of Various Active Esters Of N-Methyl Piperazine Via Trifluroacetate Ester Scheme For The Synthesis Of Various Active Esters Of N-Methyl Piperazine Via Trifluoroacetate Esters 2-Plex Phosphopeptide Screen

Figure 6b

Phosphopeptides found in 2-Plex
Phosphopeptide Screening workflow

| Peptide | QTRAP®[1] | Carr et al.[2] | iTRAQ™ -IMAC | SEQ ID NO |
|---|---|---|---|---|
| VPQLEIVPNSAEER  (S1) | YES | YES | YES | 1 |
| YKVPQLEIVPNSAEER | YES | YES | YES | 2 |
| KYKVPQLEIVPNSAEER | NO | NO | YES | 3 |
| DIGSESTEDQAMEDIK +/-Ox | YES | YES | YES | 4 |
| QMEAESISSSEEIVPNSVEQK +/-Ox | NO | YES | YES | 5 |
| EQLSTSEENSK  (S2) | NO | NO | YES | 6 |
| EQLSTSEENSKK | NO | YES | YES | 7 |
| TVDMESTEVFTK (+/-Ox) | YES | YES | YES | 8 |
| TVDMESTEVFTKK (+/-Ox) | YES | NO | YES | 9 |
| KTVDMESTEVFTK (+/-Ox) | NO | NO | YES | 10 |
| NANEEEYSIGSSSEESAEVATEEVK | NO | NO | YES | 11 |
| NAVPITPTLNREQLSTSEENSKK | NO | NO | YES | 12 |
| (K)NTMEHVSSSEESIISQETYK | NO | NO | YES | 13 |
| NMAINPSKENLC*STFC*K | YES | NO | NO | 14 |
| YIGYLEIVPNSAEER | YES | NO | NO | 15 |

```
                              SEQUENCE LISTING

<160> NUMBER OF SEQ ID NOS: 16

<210> SEQ ID NO 1
<211> LENGTH: 14
<212> TYPE: PRT
<213> ORGANISM: Artificial sequence
<220> FEATURE:
<223> OTHER INFORMATION: Fragment of bovine a-casein

<400> SEQUENCE: 1

Val Pro Gln Leu Glu Ile Val Pro Asn Ser Ala Glu Glu Arg
1               5                   10

<210> SEQ ID NO 2
<211> LENGTH: 16
<212> TYPE: PRT
<213> ORGANISM: Artificial sequence
<220> FEATURE:
<223> OTHER INFORMATION: Fragment of bovine a-casein

<400> SEQUENCE: 2

Tyr Lys Val Pro Gln Leu Glu Ile Val Pro Asn Ser Ala Glu Glu Arg
1               5                   10                  15

<210> SEQ ID NO 3
<211> LENGTH: 17
<212> TYPE: PRT
<213> ORGANISM: Artificial sequence
<220> FEATURE:
<223> OTHER INFORMATION: Fragment of bovine a-casein

<400> SEQUENCE: 3

Lys Tyr Lys Val Pro Gln Leu Glu Ile Val Pro Asn Ser Ala Glu Glu
1               5                   10                  15

Arg

<210> SEQ ID NO 4
<211> LENGTH: 16
<212> TYPE: PRT
<213> ORGANISM: Artificial sequence
<220> FEATURE:
<223> OTHER INFORMATION: Fragment of bovine a-casein

<400> SEQUENCE: 4

Asp Ile Gly Ser Glu Ser Thr Glu Asp Gln Ala Met Glu Asp Ile Lys
1               5                   10                  15

<210> SEQ ID NO 5
<211> LENGTH: 21
<212> TYPE: PRT
<213> ORGANISM: Artificial sequence
<220> FEATURE:
<223> OTHER INFORMATION: Fragment of bovine a-casein

<400> SEQUENCE: 5

Gln Met Glu Ala Glu Ser Ile Ser Ser Ser Glu Glu Ile Val Pro Asn
1               5                   10                  15
```

-continued

```
Ser Val Glu Gln Lys
            20

<210> SEQ ID NO 6
<211> LENGTH: 11
<212> TYPE: PRT
<213> ORGANISM: Artificial sequence
<220> FEATURE:
<223> OTHER INFORMATION: Fragment of bovine a-casein

<400> SEQUENCE: 6

Glu Gln Leu Ser Thr Ser Glu Glu Asn Ser Lys
1               5                   10

<210> SEQ ID NO 7
<211> LENGTH: 12
<212> TYPE: PRT
<213> ORGANISM: Artificial sequence
<220> FEATURE:
<223> OTHER INFORMATION: Fragment of bovine a-casein

<400> SEQUENCE: 7

Glu Gln Leu Ser Thr Ser Glu Glu Asn Ser Lys Lys
1               5                   10

<210> SEQ ID NO 8
<211> LENGTH: 12
<212> TYPE: PRT
<213> ORGANISM: Artificial sequence
<220> FEATURE:
<223> OTHER INFORMATION: Fragment of bovine a-casein

<400> SEQUENCE: 8

Thr Val Asp Met Glu Ser Thr Glu Val Phe Thr Lys
1               5                   10

<210> SEQ ID NO 9
<211> LENGTH: 13
<212> TYPE: PRT
<213> ORGANISM: Artificial sequence
<220> FEATURE:
<223> OTHER INFORMATION: Fragment of bovine a-casein

<400> SEQUENCE: 9

Thr Val Asp Met Glu Ser Thr Glu Val Phe Thr Lys Lys
1               5                   10

<210> SEQ ID NO 10
<211> LENGTH: 13
<212> TYPE: PRT
<213> ORGANISM: Artificial sequence
<220> FEATURE:
<223> OTHER INFORMATION: Fragment of bovine a-casein

<400> SEQUENCE: 10

Lys Thr Val Asp Met Glu Ser Thr Glu Val Phe Thr Lys
1               5                   10

<210> SEQ ID NO 11
<211> LENGTH: 25
<212> TYPE: PRT
<213> ORGANISM: Artificial sequence
<220> FEATURE:
<223> OTHER INFORMATION: Fragment of bovine a-casein

<400> SEQUENCE: 11
```

```
Asn Ala Asn Glu Glu Tyr Ser Ile Gly Ser Ser Glu Glu Ser
1               5                   10                  15

Ala Glu Val Ala Thr Glu Val Lys
            20                  25

<210> SEQ ID NO 12
<211> LENGTH: 23
<212> TYPE: PRT
<213> ORGANISM: Artificial sequence
<220> FEATURE:
<223> OTHER INFORMATION: Fragment of bovine a-casein

<400> SEQUENCE: 12

Asn Ala Val Pro Ile Thr Pro Thr Leu Asn Arg Glu Gln Leu Ser Thr
1               5                   10                  15

Ser Glu Glu Asn Ser Lys Lys
            20

<210> SEQ ID NO 13
<211> LENGTH: 21
<212> TYPE: PRT
<213> ORGANISM: Artificial sequence
<220> FEATURE:
<223> OTHER INFORMATION: Fragment of bovine a-casein

<400> SEQUENCE: 13

Lys Asn Thr Met Glu His Val Ser Ser Ser Glu Glu Ser Ile Ile Ser
1               5                   10                  15

Gln Glu Thr Tyr Lys
            20

<210> SEQ ID NO 14
<211> LENGTH: 17
<212> TYPE: PRT
<213> ORGANISM: Artificial sequence
<220> FEATURE:
<223> OTHER INFORMATION: Fragment of bovine a-casein

<400> SEQUENCE: 14

Asn Met Ala Ile Asn Pro Ser Lys Glu Asn Leu Cys Ser Thr Phe Cys
1               5                   10                  15

Lys

<210> SEQ ID NO 15
<211> LENGTH: 15
<212> TYPE: PRT
<213> ORGANISM: Artificial sequence
<220> FEATURE:
<223> OTHER INFORMATION: Fragment of bovine a-casein

<400> SEQUENCE: 15

Tyr Ile Gly Tyr Leu Glu Ile Val Pro Asn Ser Ala Glu Glu Arg
1               5                   10                  15

<210> SEQ ID NO 16
<211> LENGTH: 11
<212> TYPE: PRT
<213> ORGANISM: Artificial sequence
<220> FEATURE:
<223> OTHER INFORMATION: Non-phosphopeptide

<400> SEQUENCE: 16

Ala Leu Asn Glu Ile Asn Gly Phe Tyr Gln Lys
1               5                   10
```

US 7,868,547 B2

DETERMINATION OF ANALYTE CHARACTERISTICS BASED UPON BINDING PROPERTIES

CROSS REFERENCE TO RELATED APPLICATIONS

This application claims the benefit of U.S. Provisional Application No. 60/549,049, filed on Mar. 1, 2004, incorporated herein by reference for any purpose.

FIELD OF THE INVENTION

Embodiments of the present invention relate to the determination of analyte characteristics based upon binding properties using mass analysis and differential tagging reagents.

DESCRIPTION

1. Introduction

Embodiments of this invention can utilize isobaric and/or isomeric labeling reagents as differential labeling reagents to thereby produce labeled analytes, or labeled fragments of the analytes. One or more samples, or sample fractions, can be separated, or applied to a stationary phase (e.g. an affinity support), for the purpose of separating certain sample components based upon one or more characteristics of interest. The fractions obtained from the separation or separations can be labeled in a judiciously chosen manner with different reagents of a set of isobaric and/or isomeric labeling reagents to thereby encode some or all of the fractions for subsequent analysis. One or more samples comprising labeled analytes, or labeled fragments of the analytes, can be analyzed each individually or, in some embodiments, two or more samples can be mixed and analyzed in multiplex mode. Samples or mixtures comprising the labeled analytes can be optionally further separated and then analyzed by mass spectrometry. Daughter fragment ions of the analytes can be used to identify each analyte of the sample. Analysis of the labels, or fragment ions thereof, of the labeled analytes can be used to quantify (relative or absolute) the analyte in each of the samples, or sample fractions, used to produce a sample mixture. In this way information about the components of one or more samples of interest (including complex samples) can be interrogated for a components having the characteristic or characteristics of interest. This process can be particularly useful for the analysis of post-translational modifications of proteins and peptides in complex samples, such as those analyzed when performing proteome analysis.

2. BRIEF DESCRIPTION OF THE DRAWINGS

FIG. 1b illustrates the theoretical results of signature ion peaks in a (MS/MS) mass spectrum for the analysis represented by the workflow of FIG. 1a.

FIG. 2b illustrates the theoretical results of signature ion peaks in a (MS/MS) mass spectrum for the analysis represented by the workflow of FIG. 2a.

FIG. 3b illustrates the theoretical results of signature ion peaks in a (MS/MS) mass spectrum for the analysis represented by the workflow of FIG. 3a.

FIG. 6b is a table of experimental vs. published data associated with the analysis of a mode phosphoprotein.

3. DEFINITIONS

Figure 1A:
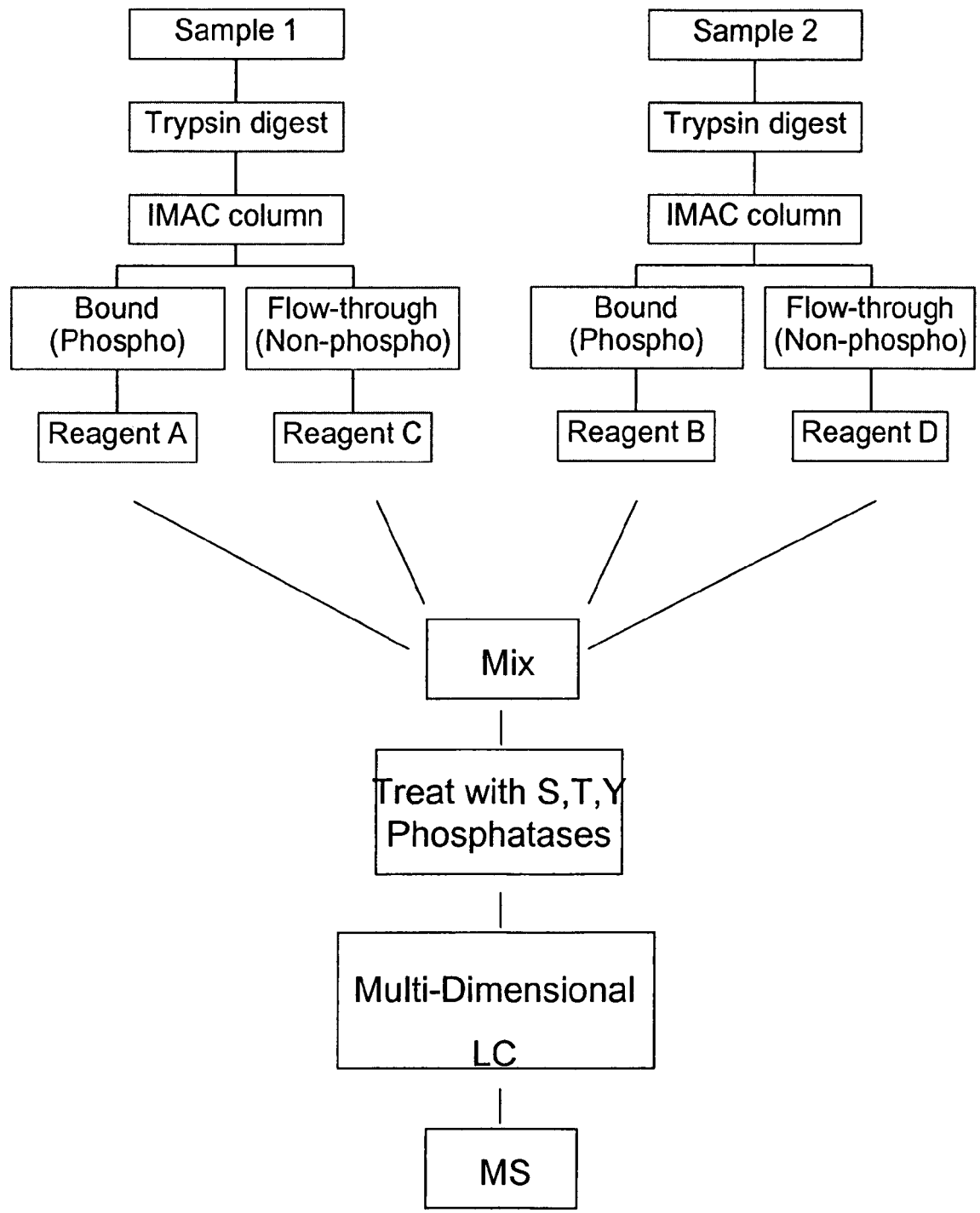
FIG. 1a illustrates the workflow for one embodiment of the analysis of theoretical Sample 1 and Sample 2 for the presence of phosphopeptides.

For the purposes of interpreting of this specification, the following definitions will apply and whenever appropriate, terms used in the singular will also include the plural and vice versa. In the event that any definition set forth below conflicts with any document incorporated herein by reference, the definition set forth below shall control.

a. As used herein, "analyte" refers to a molecule of interest that may be determined. Non-limiting examples of analytes can include, but are not limited to, proteins, peptides, antibodies, nucleic acids (both DNA or RNA), carbohydrates, lipids, steroids and/or other small molecules with a molecular weight of less than 1500 daltons. Non-limiting examples of sources for the analyte, or the sample comprising the analyte, include but are not limited to cells or tissues, or cultures (or subcultures) thereof. Non-limiting examples of cellular analyte sources include, but are not limited to, crude or processed cell lysates (including whole cell lysates), body fluids, tissue extracts or cell extracts. Still other non-limiting examples of sources for the analyte include but are not limited to fractions from a separations process such as a chromatographic separation or an electrophoretic separation. Body fluids include, but are not limited to, blood, urine, feces, spinal fluid, cerebral fluid, amniotic fluid, lymph fluid or a fluid from a glandular secretion. By processed cell lysate we mean that the cell lysate is treated, in addition to the treatments needed to lyse the cell, to thereby perform additional processing of the collected material. For example, the sample can be a cell lysate, or fraction thereof, comprising one or more analytes that are peptides formed by treatment of the total protein component of a crude cell lysate with a proteolytic enzyme to thereby digest precursor protein or proteins. For the avoidance of doubt, the term analyte can include the original analyte and compounds derived therefrom, unless from the context a clearly contrary meaning is intended. For example, in some embodiments, the term analyte can apply to a protein as well as to the peptides derived therefrom by digestion of said protein.

b. As used herein, "cellular analyte" is an analyte of cellular origin.

c. As used herein, "fragmentation" refers to the breaking of a covalent bond.

d. As used herein, "fragment" refers to a product of fragmentation (noun) or the operation of causing fragmentation (verb).

e. It is well accepted that the mass of an atom or molecule can be approximated, often to the nearest whole number atomic mass unit or the nearest tenth or hundredth of an atomic mass unit. As used herein, "gross mass" refers to the absolute mass as well as to the approximate mass within a range where the use of isotopes of different atom types are so close in mass that they are the functional equivalent whether or not the very small difference in mass of the different isotopes types used can be detected.

For example, the common isotopes of oxygen have a gross mass of 16.0 (actual mass 15.9949) and 18.0 (actual mass 17.9992), the common isotopes of carbon have a gross mass of 12.0 (actual mass 12.00000) and 13.0 (actual mass 13.00336) and the common isotopes of nitrogen have a gross mass of 14.0 (actual mass 14.0031) and 15.0 (actual mass 15.0001). Whilst these values are approximate, one of skill in the art will appreciate that if one uses the 18O isotope in one reporter of a set, the additional 2 mass units (over the isotope of oxygen having a gross mass of 16.0) can, for example, be compensated for in a different reporter of the set comprising $^{16}O$ by incorporating, elsewhere in the reporter, two carbon $^{13}C$ atoms, instead of two $^{12}C$ atoms, two $^{15}N$ atoms, instead of two $^{14}N$ atoms or even one $^{13}C$ atom and one $^{15}N$ atom, instead of a $^{12}C$ and a $^{14}N$, to compensate for the $^{18}O$. In this way the two different reporters of the set are the functional mass equivalent (i.e. have the same gross mass) since the very small actual differences in mass between the use of two $^{13}C$ atoms (instead of two $^{12}C$ atoms), two $^{15}N$ atoms (instead of two $^{14}N$ atoms), one $^{13}C$ and one $^{15}N$ (instead of a $^{12}C$ and $^{14}N$) or one $^{18}O$ atom (instead of one $^{16}O$ atom), to thereby achieve an increase in mass of two Daltons, in all of the labels of the set or kit, is not an impediment to the nature of the analysis.

f. As used herein, "labeling reagent" refers to a moiety suitable to mark an analyte for determination. The term label is synonymous with the terms tag and mark and other equivalent terms and phrases. For example, a labeled analyte can also be referred to as a tagged analyte or a marked analyte. Accordingly the terms "label", "tag", "mark" and derivatives of these terms, are interchangeable and refer to a moiety suitable to mark, or that has marked, an analyte for determination.

g. As used herein, "support", "solid support" or "solid carrier" means any solid phase material. Solid support encompasses terms such as "resin", "synthesis support", "solid phase", "surface" "membrane" and/or "support". A solid support can be composed of organic polymers such as polystyrene, polyethylene, polypropylene, polyfluoroethylene, polyethyleneoxy, and polyacrylamide, as well as co-polymers and grafts thereof. A solid support can also be inorganic, such as glass, silica, controlled-pore-glass (CPG), or reverse-phase silica. The configuration of a solid support can be in the form of beads, spheres, particles, granules, a gel, a membrane or a surface. Surfaces can be planar, substantially planar, or non-planar. Solid supports can be porous or non-porous, and can have swelling or non-swelling characteristics. A solid support can be configured in the form of a well, depression or other container, vessel, feature or location. A plurality of solid supports can be configured in an array at various locations, addressable for robotic delivery of reagents, or by detection methods and/or instruments.

h. As used herein, "stationary phase" refers to a support used to differentially bind one or more component analytes of a sample, or fraction thereof. One non-limiting example of a stationary phase is a chromatography packing material. Sources for chromatography packing materials are well known in the art. The function of and methods of utilizing chromatography packing materials to effect separations are well known in the art.

i. As used herein, "natural isotopic abundance" refers to the level (or distribution) of one or more isotopes found in a compound based upon the natural prevalence of an isotope or isotopes in nature. For example, a natural compound obtained from living plant matter will typically contain about 1.08% $^{13}C$ relative to $^{12}C$ j. As used herein, "sample, or a fraction thereof" or "sample fraction" can be used to refer to a fraction of a sample. The fraction of the sample can be generated either by simply withdrawing a fraction of a sample or else it can be generated by performing a separations process that results in the sample being fractionated into two or more fractions. Unless, the content of the description indicates otherwise, these references are interchangeable and refer to either type of creation of a fraction (or portion) of a sample.

k. As used herein, "signature ion" refers to the unique ion produced by a fragment (i.e. the reporter) of each unique labeling reagent of a set of isomeric and/or isobaric labeling reagents. The signature ion or reporter (or reporter ion) identifies the unique labeling reagent and its peak intensity correlates with the amount of labeled analyte present in the sample that is analyzed. The signature ion is sometimes also referred to as a reporter or reporter ion and vice versa.

4. GENERAL

Figure 4:
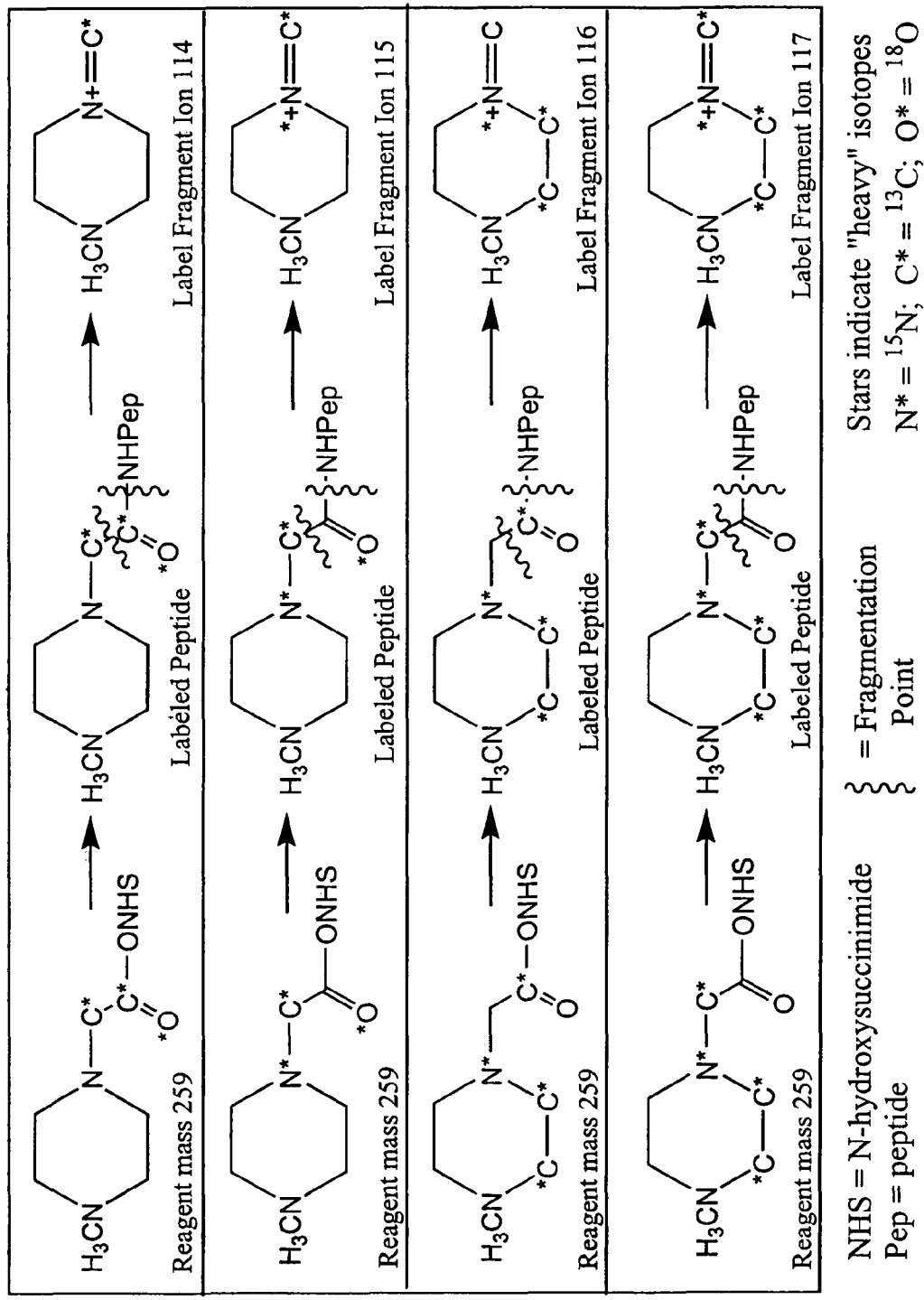
FIG. 4 illustrates one possible set of four isobaric labeling reagents suitable for use with the embodiments of this invention.
Figure 5A:
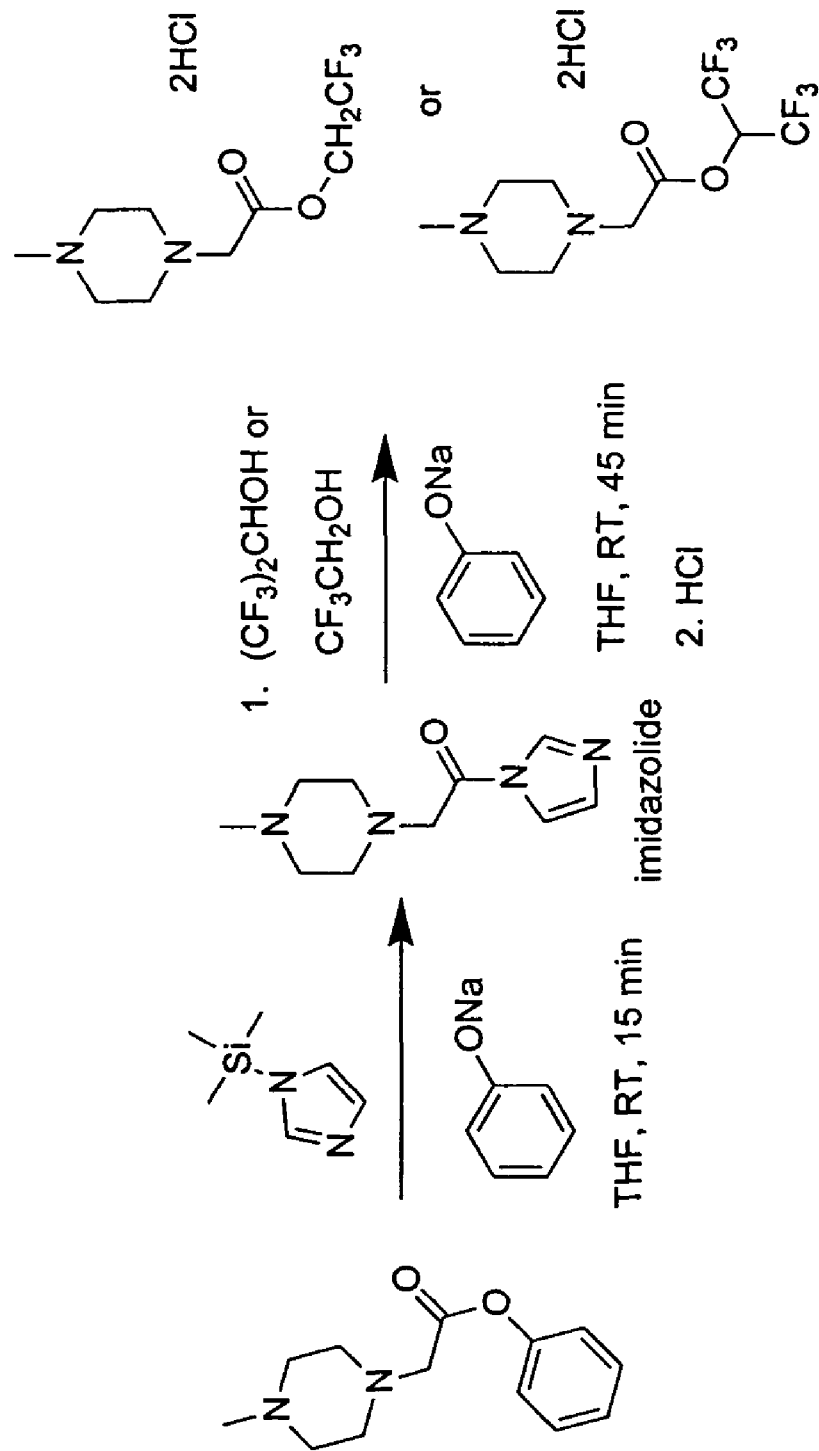
FIG. 5A illustrates a scheme for the synthesis of various active esters.
Figure 5B:
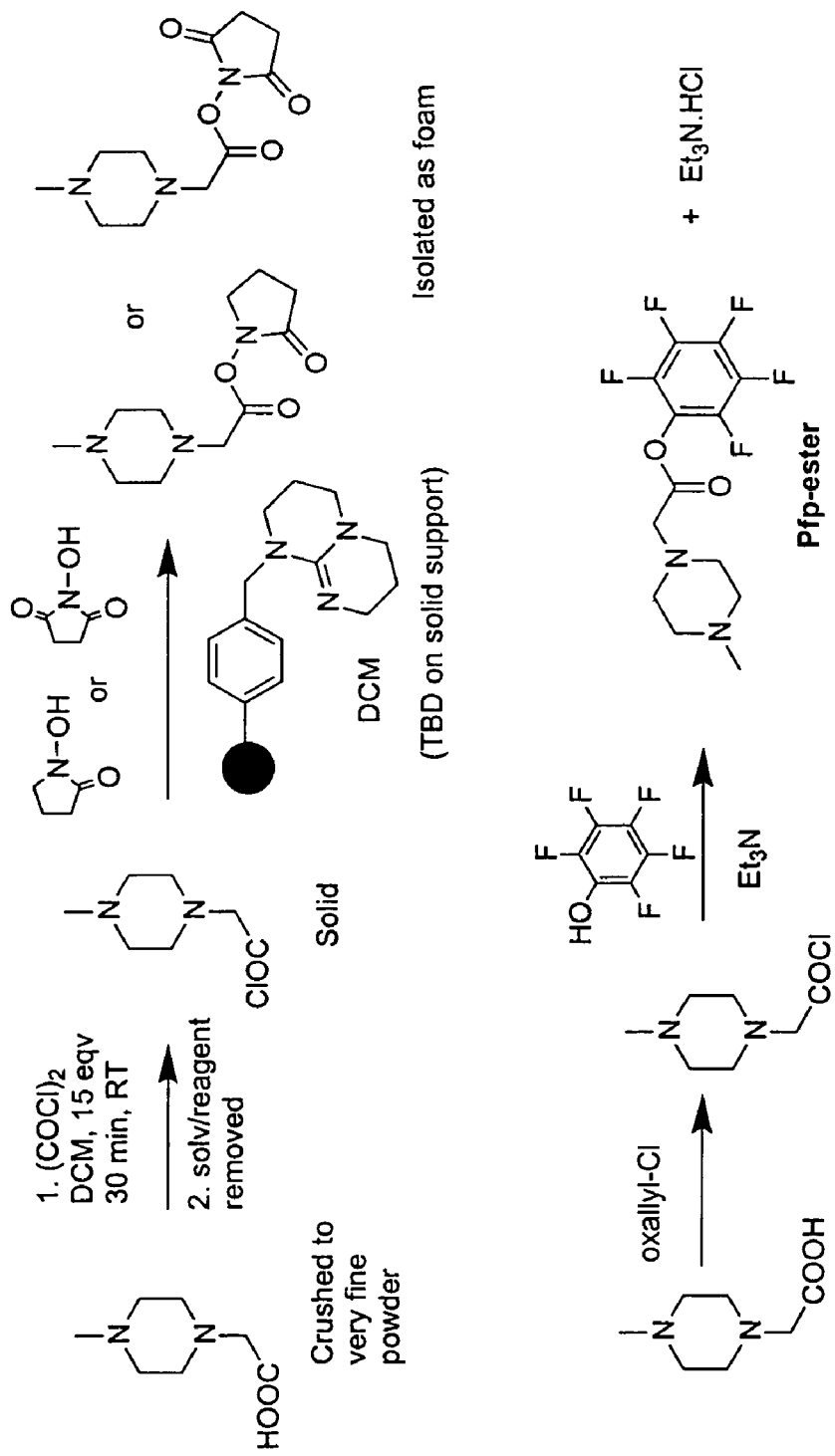
FIG. 5B illustrates another scheme for the synthesis of various active esters.
Figure 5C:
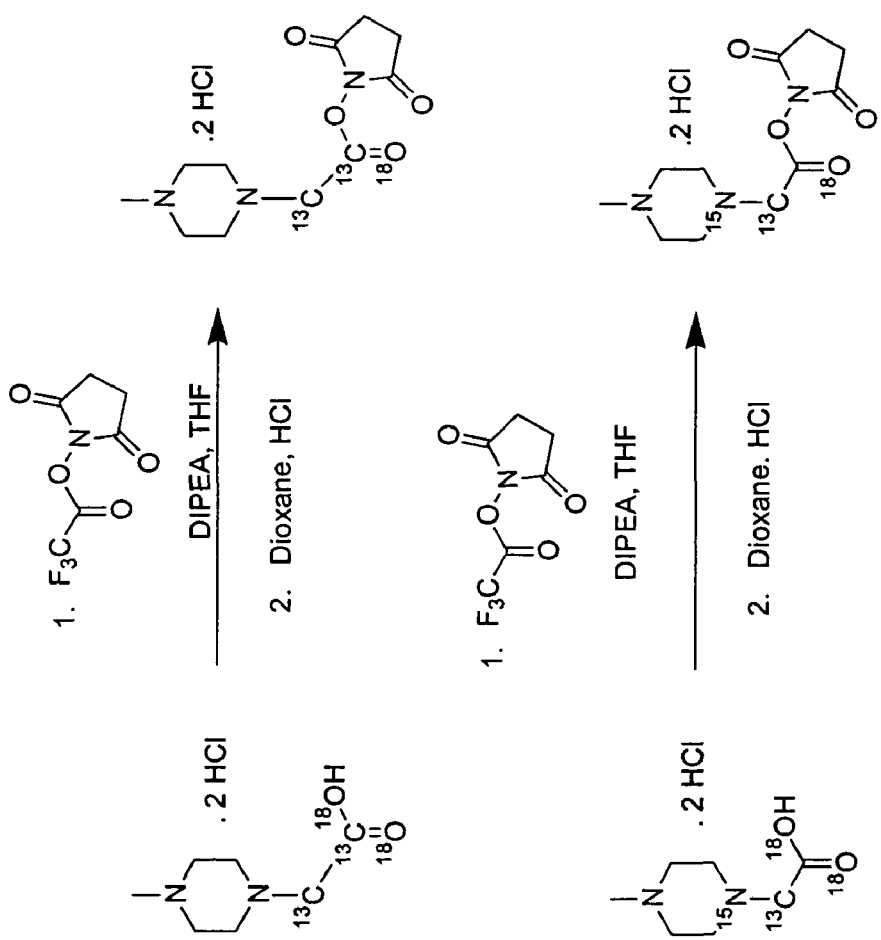
FIG. 5C illustrates still another scheme for the synthesis of various active esters.
Figure 5D:
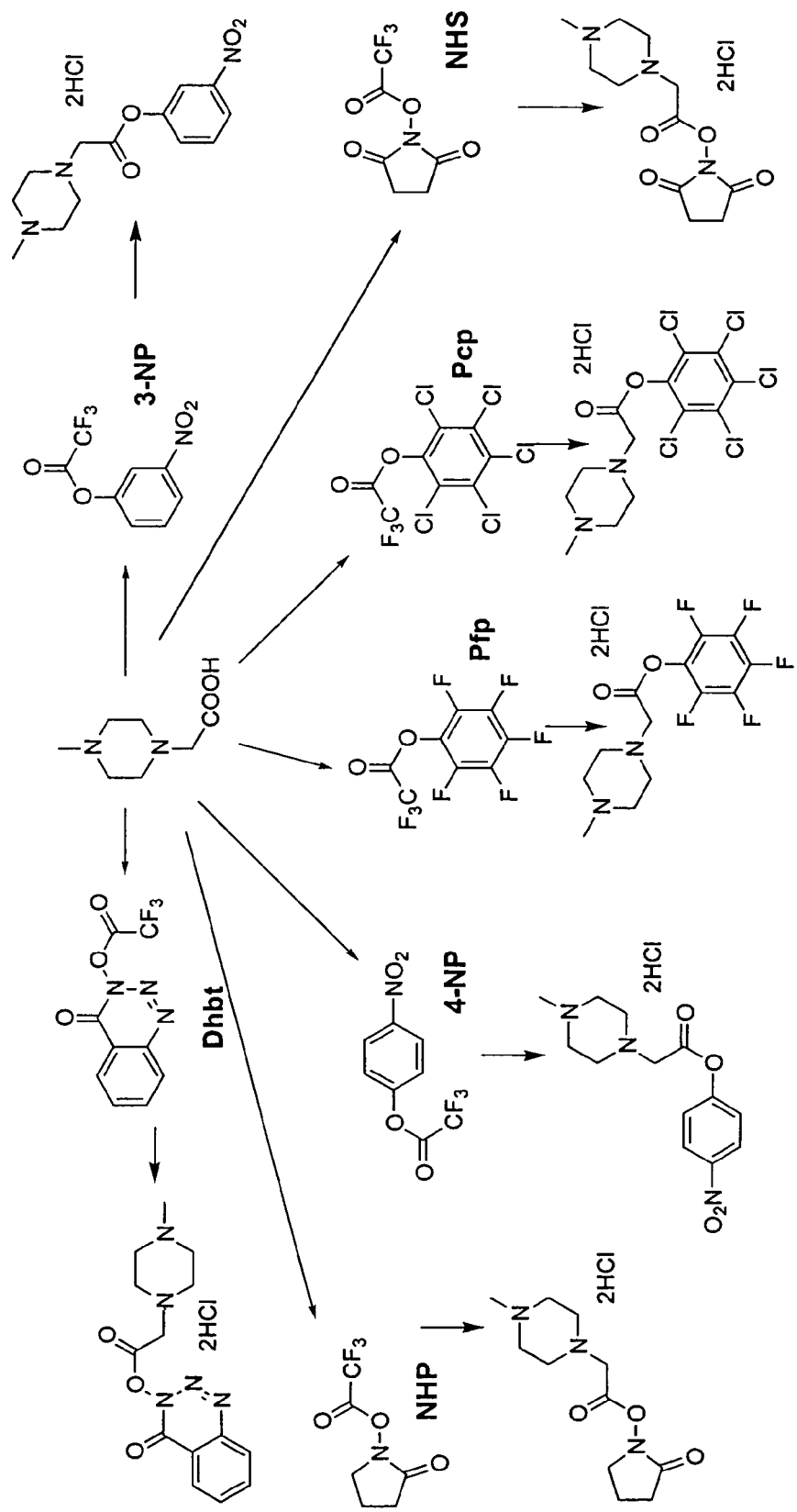
FIG. 5D illustrates yet another scheme for the synthesis of various active esters.

Labeling Reagents:

Labeling reagents used in embodiments of this invention can be isobaric and/or isomeric compositions. Typically, a set of isomeric or isobaric labeling reagents can be used. Labeling reagents of a set can be selected to comprise a reporter that is unique and can be independently determined, for example in MS/MS analysis. The isobaric and/or isomeric labeling reagents can be those disclosed in WO2004/070352, incorporated by reference for any and all purposes. The isobaric and/or isomeric labeling reagents can be those disclosed in copending and commonly owned U.S. patent application Ser. Nos. 10/765,458, 10/765,264, 10/765,267 or 10/765,458, all of which are herein incorporated by reference for any and all purposes. The isobaric and/or isomeric labeling reagents can be polymer-based labeling reagents such as those described in WO02/14867 or United States Published Patent Application No. U.S. 2003-0045694A1, herein incorporated by reference for all purposes. The labeling reagents can be those isobaric or isomeric labeling reagents disclosed in WO01/68664, incorporated herein by reference for all purposes. An example of a set of four suitable isobaric reagents is illustrated in FIG. 4. Sets of isobaric labeling reagents are commercially available from Applied Biosystems and sold as iTRAQ™ labeling reagents (See: Example 4).

Isobaric labeling reagents can be useful because, except for their detectable difference upon MS/MS analysis, they can be structurally and chemically indistinguishable (except where there is a detectable difference in absolute mass, as compared with gross mass). Accordingly, the same analyte labeled with two different isobaric labeling reagents of a set will be structurally and chemically indistinguishable. Accordingly, each of the two identical analytes, each bearing a unique isobaric label, should be indistinguishable in their reactivity as well as be indistinguishable in their separations properties.

The unique reporters of the labeling reagents can be used to encode analytes of the samples, or sample fractions, as the case may be. Encoding can be performed by treatment of the sample, or sample fraction, with the labeling reagent to thereby produce labeled analyte or analytes and eventually a sample mixture can be created from the samples, or sample fractions. When the sample mixture is analyzed, the reporters can be used to decode the relative and/or absolute amount (often reported in concentration or quantity) of each analyte in the different samples, or sample fractions, used to formulate the sample mixture. The analytes themselves can also be determined from daughter ion analysis. In this way, components of the complex sample mixture are determined in a multiplex fashion and the analysis provides information (i.e. analyte identity and quantity) that relates back to the original samples and/or fractions thereof.

Labeling the Analytes of a Sample:

The labeling reagents will comprise a reactive group. The reactive group of the labeling reagent or reagents used in the embodiments of the invention can be either an electrophile or a nucleophile that is capable of reacting with one or more reactive analytes of a sample. The reactive group can be preexisting or it can be prepared in-situ. In some embodiments, in-situ preparation of the reactive group can proceed in the absence of the reactive analyte. In some embodiments, in-situ preparation can proceed in the presence of the reactive analyte. For example, a carboxylic acid group can be modified in-situ with water-soluble carbodiimide (e.g. 1-(3-dimethylaminopropyl)-3-ethylcarbodiimide hydrochloride; EDC) to thereby prepare an electrophilic group that can be reacted with a nucleophile such as an amine group (including an aryl amine group). In some embodiments, activation of the carboxylic acid group of a labeling reagent with EDC can be performed in the presence of an amine (nucleophile) containing analyte. Alternatively, the amine (nucleophile) containing analyte can also be added after the initial reaction with EDC is performed. In other embodiments, the reactive group can be generated in-situ by the in-situ removal of a protecting group. Consequently, any existing or newly created reagent or reagents that can effect the derivatization of analytes by the reaction of nucleophiles and/or electrophiles are contemplated by the method, mixture, kit and/or composition embodiments of this invention.

Where the reactive group of the labeling reagent is an electrophile, it can react with a suitable nucleophilic group of the analyte or analytes. Where the reactive group of the labeling reagent is a nucleophile, it can react with a suitable electrophilic group of the analyte or analytes. Numerous pairs of suitable nucleophilic groups and electrophilic groups are known and often used in the chemical and biochemical arts. Non-limiting examples of reagents comprising suitable nucleophilic or electrophilic groups that can be coupled to analytes (e.g. such as proteins, peptides, nucleic acids, carbohydrates, lipids, steroids or other small molecules of less that 1500 daltons) to effect their derivatization, are described in the Pierce Life Science & Analytical Research Products Catalog & Handbook (a Perstorp Biotec Company), Rockford, Ill. 61105, USA. Other suitable reagents are well known in the art and are commercially available from numerous other vendors such as Sigma-Aldrich.

The reactive group of a labeling reagent can be an amine reactive group. For example the amine reactive group can be an active ester. Active esters are well known in peptide synthesis and refer to certain esters that are easily reacted with the N-α amine of an amino acid under conditions commonly used in peptide synthesis. The amine reactive active ester can be an N-hydroxysuccinimidyl ester, a N-hydroxysulfosuccinimidyl ester, a pentafluorophenyl ester, a 2-nitrophenyl ester, a 4-nitrophenyl ester, a 2,4-dinitrophenylester or a 2,4-dihalophenyl ester. For example, the alcohol or thiol group of an active ester can have the formula:

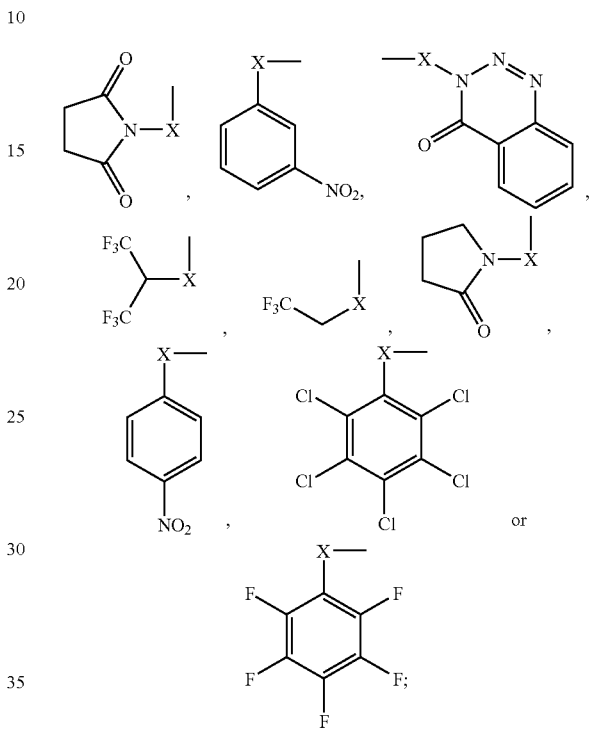

wherein X is O or S, but preferably O. All of the foregoing being alcohol or thiol groups known to form active esters in the field of peptide chemistry wherein said alcohol or thiol group is displaced by the reaction of the N-α-amine of the amino acid with the carbonyl carbon of the ester. It should be apparent that the active ester (e.g. N-hydroxysuccinimidyl ester) of any suitable labelling/tagging reagent described herein could be prepared using well-known procedures (See: Greg T. Hermanson (1996). "The Chemistry of Reactive Groups" in "Bioconjugate Techniques" Chapter 2 pages 137-165, Academic Press, (New York); also see: Innovation And Perspectives In Solid Phase Synthesis, Editor: Roger Epton, SPCC (UK) Ltd, Birmingham, 1990). Methods for the formation of active esters of N-substituted piperazine acetic acids compounds that are representative examples of labelling reagents of the general formula: RP-X-LK-Y-RG, are described in co-pending and commonly owned U.S. patent application Ser. No. 10/751,354, incorporated herein by reference for all purposes. FIGS. 5A, 5B, 5C and 5D are illustrations of various methods for preparing active esters of N-methyl piperazine. Using no more than routine experimentation, such general methods can be applied to the preparation of other types of active esters as well as to the preparation of active esters of other labelling reagents. Methods for labelling peptide and protein analytes have been described for the iTRAQ™ reagents available from Applied Biosystems.

In another embodiment, the reactive group of the labelling reagent can be a mixed anhydride since mixed anhydrides are known to efficiently react with amine groups to thereby produce amide bonds.

The reactive group of a labeling reagent can be a thiol reactive group. For example, the thiol reactive group can be a malemide, an alkyl halide, an aryl halide or an α-halo-acyl. By halide or halo we mean atoms of fluorine, chlorine, bromine or iodine.

The reactive group of a labeling reagent can be a hydroxyl reactive group. For example, the hydroxyl reactive group can be a trityl-halide or a silyl-halide reactive moiety. The tritylhalide reactive moieties can be substituted (e.g. Y-methoxytrityl, Y-dimethoxytrityl, Y-trimethoxytrityl, etc) or unsubstituted wherein Y is defined below. The silyl reactive moieties can be alkyl substituted silyl halides, such as Y-dimethylsilyl, Y-ditriethylsilyl, Y-dipropylsilyl, Y-diisopropylsilyl, etc.) wherein Y is defined below.

The reactive group of the labeling reagent can be a nucleophile such as an amine group, a hydroxyl group or a thiol group.

Mass Spectrometers/Mass Spectrometry:

Embodiments of this invention can be practiced using tandem mass spectrometers and other mass spectrometers that have the ability to select and fragment molecular ions. Tandem mass spectrometers (and to a lesser degree single-stage mass spectrometers such as those that exhibit post source decay) have the ability to select and fragment molecular ions according to their mass-to-charge (m/z) ratio, and then record the resulting fragment (daughter) ion spectra. More specifically, daughter fragment ion spectra can be generated by subjecting selected ions to dissociative energy levels (e.g. by collision-induced dissociation (CID)). For example, ions corresponding to labeled peptides of a particular m/z ratio can be selected from a first mass analysis, fragmented and reanalyzed in a second (MS/MS) mass analysis. Representative instruments that can perform such tandem mass analysis include, but are not limited to, magnetic four-sector, tandem time-of-flight, triple quadrupole, ion-trap, and hybrid quadrupole time-of-flight (Q-TOF) mass spectrometers.

These types of mass spectrometers may be used in conjunction with a variety of ionization sources, including, but not limited to, electrospray ionization (ESI) and matrix-assisted laser desorption ionization (MALDI). Ionization sources can be used to generate charged species for the first mass analysis where the analytes do not already possess a fixed charge. Additional mass spectrometry instruments and fragmentation methods include post-source decay in MALDI-MS instruments and high-energy CID using MALDI-TOF (time of flight)-TOF MS. For a recent review of tandem mass spectrometers please see: R. Aebersold and D. Goodlett, *Mass Spectrometry in Proteomics. Chem. Rev.* 101: 269-295 (2001). Also see U.S. Pat. No. 6,319,476, herein incorporated by reference for all purposes, for a discussion of TOF-TOF mass analysis techniques. Generally there is no limitation on the type of mass spectrometer that can be used so long as it is possible to obtain a first mass analysis, select and fragment ions from the first mass analysis and then analyze the result of said fragmentation.

Fragmentation by Dissociative Energy Levels:

It is well accepted that bonds can fragment as a result of the processes occurring in a mass spectrometer. Moreover, bond fragmentation can be induced in a mass spectrometer by subjecting ions to dissociative energy levels. For example, the dissociative energy levels can be produced in a mass spectrometer by collision-induced dissociation (CID). Those of ordinary skill in the art of mass spectrometry will appreciate that other exemplary techniques for imposing dissociative energy levels that cause fragmentation include, but are not limited to, photo dissociation, electron capture and surface induced dissociation.

The process of fragmenting bonds by collision-induced dissociation involves increasing the kinetic energy state of selected ions to a point where bond fragmentation occurs. For example, kinetic energy can be transferred by collision with an inert gas (such as nitrogen, helium or argon) in a collision cell. The amount of kinetic energy that can be transferred to the ions is proportional to the number of gas molecules that are allowed to enter the collision cell. When more gas molecules are present, a greater amount of kinetic energy can be transferred to the selected ions, and less kinetic energy is transferred when there are fewer gas molecules present.

It is therefore clear that the dissociative energy level in a mass spectrometer can be controlled. It is also well accepted that certain bonds are more labile than other bonds. The lability of the bonds in an analyte or the reporter of the labeling reagent depends upon the nature of the analyte or the labeling reagent. Accordingly, the dissociative energy levels can be adjusted so that the analytes and/or the labels (e.g. the reporter/linker combinations) can be fragmented in a somewhat controlled manner. One of skill in the art will appreciate how to make such routine adjustments to the components of a mass spectrometer to thereby achieve the appropriate level of dissociative energy to thereby fragment at least a portion of ions of labeled analytes into ionized reporter moieties and daughter fragment ions.

For example, dissociative energy can be applied to ions that are selected/isolated from the first mass analysis. In a tandem mass spectrometer, the extracted ions can be subjected to dissociative energy levels and then transferred to a second mass analyzer. The selected ions can have a selected mass to charge ratio. The mass to charge ratio can be within a range of mass to charge ratios depending upon the characteristics of the mass spectrometer. When collision induced dissociation is used, the ions can be transferred from the first to the second mass analyzer by passing them through a collision cell where the dissociative energy can be applied to thereby produce fragment ions. For example the ions sent to the second mass analyzer for analysis can include all, or a portion, of the remaining (unfragmented) selected ions, as well as reporter ions (signature ions) and daughter fragment ions of the labeled analyte.

Analyte Determination by Computer Assisted Database Analysis:

In some embodiments, analytes can be determined based upon daughter-ion fragmentation patterns that are analyzed by computer-assisted comparison with the spectra of known or "theoretical" analytes. For example, the daughter fragment ion spectrum of a peptide ion fragmented under conditions of low energy CID can be considered the sum of many discrete fragmentation events. The common nomenclature differentiates daughter fragment ions according to the amide bond that breaks and the peptide fragment that retains charge following bond fission. Charge-retention on the N-terminal side of the fissile amide bond results in the formation of a b-type ion. If the charge remains on the C-terminal side of the broken amide bond, then the fragment ion is referred to as a y-type ion. In addition to b- and y-type ions, the CID mass spectrum may contain other diagnostic fragment ions (daughter fragment ions). These include ions generated by neutral loss of ammonia (−17 amu) from glutamine, lysine and arginine or the loss of water (−18 amu) from hydroxyl-containing amino acids such as serine and threonine. Certain amino acids have been observed to fragment more readily under conditions of low-energy CID than others. This is particularly apparent for peptides containing proline or aspartic acid residues, and even more so at aspartyl-proline bonds (Mak, M. et al., *Rapid Commun. Mass Spectrom.*, 12: 837-842 (1998)). Accordingly, the peptide bond of a Z-pro dimer or Z-asp dimer (wherein Z is any natural amino acid, pro is proline and asp is aspartic acid) will tend to be more labile as compared with the peptide bond between all other amino acid dimer combinations.

For peptide and protein samples therefore, low-energy CID spectra contain redundant sequence-specific information in overlapping b- and y-series ions, internal fragment ions from the same peptide, and immonium and other neutral-loss ions. Interpreting such CID spectra to assemble the amino acid sequence of the parent peptide de novo is challenging and time-consuming. The most significant advances in identifying peptide sequences have been the development of computer algorithms that correlate peptide CID spectra with peptide sequences that already exist in protein and DNA sequence databases. Such approaches are exemplified by programs such as SEQUEST (Eng, J. et al. *J. Am. Soc. Mass Spectrom.*, 5: 976-989 (1994)) and MASCOT (Perkins, D. et al. Electrophoresis, 20: 3551-3567 (1999)).

In brief, experimental peptide CID spectra (MS/MS spectra) are matched or correlated with 'theoretical' daughter fragment ion spectra computationally generated from peptide sequences obtained from protein or genome sequence databases. The match or correlation is based upon the similarities between the expected mass and the observed mass of the daughter fragment ions in MS/MS mode. The potential match or correlation is scored according to how well the experimental and 'theoretical' fragment patterns coincide. The constraints on databases searching for a given peptide amino acid sequence are so discriminating that a single peptide CID spectrum can be adequate for identifying any given protein in a whole-genome or expressed sequence tag (EST) database. For other reviews please see: Yates, J. R. Trends, *Genetics*, 16: 5-8 (2000) and Yates, J. R., *Electrophoresis* 19: 893-900 (1998).

Accordingly, daughter fragment ion analysis of MS/MS spectra can be used not only to determine the analyte of a labeled analyte, it can also be used to determine analytes from which the determined analyte originated. For example, identification of a peptide in the MS/MS analysis can be can be used to determine the protein from which the peptide was cleaved as a consequence of an enzymatic digestion of the protein. It is envisioned that similar analysis can be applied to the determination of other analytes, such as nucleic acids, carbohydrates, lipids and steroids.

Sample Processing:

In certain embodiments of this invention, a sample can be processed prior to, as well as after, labeling of the analytes. Processing can be applied to the whole of a sample, or a fraction thereof. Processing can be applied to sample mixtures or a fraction thereof. Processing can be used to de-complexify the sample or be used to put the sample into a better form for analysis. The processing can facilitate the labeling of the analytes. The processing can facilitate the analysis of the sample components. The processing can simplify the handling of the samples. The processing can facilitate two or more of the foregoing.

For example, a sample or sample mixture can be treated with an enzyme. The enzyme can be a protease (to degrade proteins and peptides), a nuclease (to degrade nucleic acids) or some other degrading enzyme. The enzyme can be chosen to have a very predictable degradation pattern. Two or more proteases and/or two or more nuclease enzymes may also be used together, or with other enzymes, to thereby degrade sample components.

For example, the proteolytic enzyme trypsin is a serine protease that cleaves peptide bonds between lysine or arginine and an unspecific amino acid to thereby produce peptides that comprise an amine terminus (N-terminus) and lysine or arginine carboxyl terminal amino acid (C-terminus). In this way the peptides from the cleavage of the protein are predictable and their presence and/or quantity, in a sample from a trypsin digest, can be indicative of the presence and/or quantity of the protein of their origin. Moreover, the free amine termini of a peptide can be a good nucleophile that facilitates its labeling. Other exemplary proteolytic enzymes include papain, pepsin, ArgC, LysC, V8 protease, AspN, pronase, chymotrypsin and carboxypeptidease C.

For example, a protein (e.g. protein Z) might produce three peptides (e.g. peptides B, C and D) when digested with a protease such as trypsin. Accordingly, a sample that has been digested with a proteolytic enzyme, such as trypsin, and that when analyzed is confirmed to contain peptides B, C and D, can be said to have originally comprised the protein Z (See the discussion above under the heading: "Analyte Determination By Computer Assisted Database Analysis"). The quantity of peptides B, C and O will also correlate with the quantity of protein Z in the sample that was digested. In this way, any determination of the identity and/or quantity of one or more of peptides B, C and D in a sample (or a fraction thereof), can be used to identify and/or quantify protein Z in the original sample (or a fraction thereof).

Because activity of the enzymes is predictable, the sequence of peptides that are produced from degradation of a protein of known sequence can be predicted. With this information, "theoretical" peptide information can be generated. A determination of the "theoretical" peptide fragments in computer assisted analysis of daughter fragment ions (as described above) from mass spectrometry analysis of an actual sample can therefore be used to determine one or more peptides or proteins in one or more unknown samples. It is envisioned that similar analysis can be applied to the determination of other analytes, such as nucleic acids, carbohydrates, lipids and steroids.

In some other embodiments, processing can comprise treatment with an enzyme other than those that degrade sample components. For example, the enzyme can be a phosphatase, glycosidase or other enzyme that removes a modification from the analyte, such as those caused by post-translational modification.

In some other embodiments, sample processing involves chemical treatment. The chemical treatment can be used as an alternative to, or in conjunction with, an enzyme treatment as discussed above. The chemical treatment can be selected to remove a modification of the analyte. For example, the chemical treatment can be selected to remove a modification from the analyte, such as those caused by post-translational modification.

Although not typical, the enzymatic and/or chemical treatment can be used to add one or more moieties to the analyte instead of remove a modification. For simplicity of discussion all references herein will be to removal of the modification of the analyte but it is to be understood that these references are intended to include the possibility of adding one or moieties to the analyte. What is important is that a change occurs to the analyte that can be encoded with unique labeling reagents, depending on when in the process the change to the analyte occurs.

Separations:

In some embodiments, the processing of a sample or a sample mixture comprising analytes (whether or not labeled) can involve separation. In some embodiments, the separation can involve the fractionation of a sample (or a fraction thereof) between those components of the sample that bind to a stationary phase and those components that do not. Such a process is often referred to as affinity chromatography. In some embodiments, the separation can involve the fractionation of the sample or sample mixture based upon relative affinities of the components of the sample or sample mixture (or a fraction or fractions thereof).

In some embodiments, a separation can be performed to distinguish those components of a sample or sample mixture that bind to a certain stationary phase from those that do not. For example, phosphopeptides are known to bind to immobilized-metal affinity chromatography (IMAC) columns. In this way, phosphorylated peptides of a sample can be separated from non-phosphorylated peptides. Other types of supports can be used to effect the separation of analytes of a complex sample based upon other types of affinity characteristics.

In some embodiments, a sample mixture comprising differentially labeled analytes from the same or different samples can be prepared. By differentially labeled we mean that each of the labels comprises a unique property that can be identified (e.g. comprises a unique reporter moiety that produces a unique "signature ion" in MS/MS analysis). In order to analyze the sample mixture, components of the sample mixture can be separated and mass analysis performed on the sample mixture, or a fraction thereof. In this way, the complexity of the analysis can be substantially reduced since separated analytes can be individually analyzed for mass thereby increasing the sensitivity of the analysis process. The analysis can be repeated one or more times on one or more additional fractions of the sample mixture to thereby allow for the analysis of all fractions of the sample mixture.

Separation conditions under which identical analytes that are differentially labeled co-elute at a concentration, or in a quantity, that is in proportion to their abundance in the sample mixture can be used to determine the amount of each labeled analyte in each of the samples that comprise the sample mixture provided that the amount of each sample added to the sample mixture is known. Accordingly, in some embodiments, separation of the sample mixture can simplify the analysis whilst maintaining the correlation between signals determined in the mass analysis (e.g. MS/MS analysis) with the amount of the differently labeled analytes in the sample mixture.

Separations can be performed by chromatography. For example, liquid chromatography/mass spectrometry (LC/MS) can be used to effect such a sample separation and mass analysis. Moreover, any chromatographic separation process suitable to separate the analytes of interest can be used. For example, the chromatographic separation can be normal phase chromatography, reversed-phase chromatography, ion-exchange chromatography, size exclusion chromatography or affinity chromatography.

Separations can be performed electrophoretically. Non-limiting examples of electrophoretic separations techniques that can be used include, but are not limited to, 1D electrophoretic separation, 2D electrophoretic separation and/or capillary electrophoretic separation.

An isobaric labeling reagent or a set of reagents can be used to label the analytes of a sample. Isobaric labeling reagents are particularly useful when a separation step is performed because the isobaric labels of a set of labeling reagents are structurally and chemically indistinguishable (and can be indistinguishable by gross mass until fragmentation removes the reporter from the analyte). Thus, all analytes of identical composition that are labeled with different isobaric labels can chromatograph in exactly the same manner (i.e. co-elute). Because they are structurally and chemically indistinguishable, the eluent from the separation process can comprise an amount of each isobarically labeled analyte that is in proportion to the amount of that labeled analyte in the sample mixture. Furthermore, from the knowledge of how the sample mixture was prepared (portions of samples, an other optional components (e.g. calibration standards) added to prepare the sample mixture), it is possible to relate (e.g. back calculate) the amount of labeled analyte in the sample mixture back to the amount of that labeled analyte in the sample, or sample fraction, from which it originated.

The labeling reagents can also be isomeric. Although isomers can sometimes be chromatographically separated, there are circumstances, that are condition dependent, where the separation process can be operated to co-elute all of the identical analytes that are differentially labeled wherein the amount of all of the labeled analytes exist in the eluent in proportion to their concentration and/or quantity in the sample mixture.

As used herein, isobars differ from isomers in that isobars are structurally and chemically indistinguishable compounds (except for isotopic content and/or distribution) of the same nominal gross mass whereas isomers are structurally and/or chemically distinguishable compounds of the same nominal gross mass.

Relative and Absolute Quantification of Analytes:

The relative quantitation of differentially labeled identical analytes of a sample mixture is possible using sets of isobaric and/or isomeric labeling reagents. Relative quantitation of differentially labeled identical analytes is possible by comparison of the relative amounts of reporter (e.g. area or height of the peak reported) that are determined in the second (MS/MS) mass analysis for a selected, labeled analyte observed in a first (MS) mass analysis. Put differently, where each reporter can be correlated with information for a particular sample (or sample fraction) used to produce a sample mixture, the relative amount of that reporter, with respect to other reporters observed in the second mass analysis, is the relative amount of that analyte in the sample mixture. Where the amount of each sample, or fraction thereof, used to compose the sample mixture is known, the relative amount of the analyte in each sample used to prepare the sample mixture can be back calculated based upon the relative amount of reporter observed for the ions of the labeled analyte selected from the first mass analysis. This process can be repeated for all of the different labeled analytes observed in the first mass analysis. In this way, it is possible that the relative amount (often expressed in terms of concentration and/or quantity) of each reactive analyte, in each of the different samples (or sample fractions) used to produce the sample mixture, can be determined.

In some embodiments, absolute quantitation of analytes can be determined. For these embodiments, a known amount of one or more differentially labeled analytes (the calibration standard or calibration standards) can be added to the sample mixture. A calibration standard can be an expected analyte that is labeled with an isomeric or isobaric label of the set of labels used to label the analytes of the sample mixture provided that the reporter for the calibration standard is unique as compared with any of the samples used to form the sample mixture. Once the relative amount of reporter (i.e. signature ion) for the calibration standard, or standards, is determined with relation to the relative amounts of the reporter for the differentially labeled analytes of the sample mixture, it is possible to calculate the absolute amount (often expressed in concentration and/or quantity) of all of the differentially labeled analytes in the sample mixture. In this way, the absolute amount of each differentially labeled analyte (for which there is a calibration standard in the sample from which the analyte originated) can also be determined based upon the knowledge of how the sample mixture was prepared.

Notwithstanding the foregoing, corrections to the intensity of the reporters (signature ions) can be made, as appropriate, for any naturally occurring, or artificially created, isotopic abundance within the reporters. An example of such a correction methodology can also be found in copending and co-owned U.S. patent application Ser. No. 10/916,629, entitled: "Method and Apparatus For De-Convoluting A Convoluted Spectrum", filed on Aug. 12, 2004, and herein incorporated by reference for any purpose. The more care taken to accurately quantify the intensity of each reporter, the more accurate will be the relative and absolute quantification of the analytes in the original samples, or sample fractions, used to compose the sample mixture.

In brief, using these methods, the intensity of up mass and down mass isotope peaks associated with a particular signature ion can be added to the major intensity peak associated with the signature ion (i.e. the reporter) so that the contribution of all intensities are properly attributed to the correct reporter. Peak intensities not associated with a particular signature ion are deducted as appropriate. By fully allocating all peak intensities to the proper signature ions, the relative and absolute quantification information associated with a signature ion can be quite accurate.

Proteomic Analysis:

Samples can be multiplexed (i.e. by creating sample mixtures), analyzed and reanalyzed in a rapid and repetitive manner using mass analysis techniques. For example, sample mixtures can be analyzed for the amount of individual analytes in one or more samples. The amount (often expressed in concentration and/or quantity) of those analytes can be determined for the samples (or sample fractions) from which the sample mixture was composed. Because the sample processing and mass analyses can be performed rapidly, these methods can be repeated numerous times so that the amount of many differentially labeled analytes of the sample mixture can be determined with regard to their relative and/or absolute amounts in the sample from which the analyte originated.

One application where such a rapid multiplex analysis is useful is in the area of proteomic analysis. Proteomics can be viewed as an experimental approach to describe the information encoded in genomic sequences in terms of structure, function and regulation of biological processes. This may be achieved by systematic analysis of the total protein component expressed by a cell or tissue. Mass spectrometry, used in combination with embodiments of this invention, is one possible tool for such global protein analysis, including the analysis of post-translational modifications, pull downs or other such complex analyses. The methods can also be used for biomarker analysis or for time course analysis.

5. VARIOUS MODES OF PRACTICING THE INVENTION

Embodiments of this invention permit the analysis of one or more samples of interest for the presence and/or absence of modified and unmodified analytes where the modification can be of interest. Chromatographic techniques (e.g. affinity chromatography) can be used to separate modified analytes from the unmodified analytes. In some embodiments, the presence of the modification can be independently confirmed by distinguishing between specific and non-specific interactions with an affinity support. Isobaric and/or isomeric labeling reagents of a set can be used to encode the analytes of the different samples, or sample fractions. The relative amounts of the modified and unmodified analytes in the various samples can be determined from the ratios of the reporters (signature ions) associated with the various labeling reagents and optionally, absolute quantitation is possible if labeled (calibration) standards are used. Generally, the modified and unmodified analytes of one or more samples can be determined according to the following general procedure.

Samples to be determined are selected and can be optionally processed when desired. Exemplary embodiments of sample processing were previously discussed under the heading: "Sample Processing". For example, if the analytes to be determined are proteins, it may be desirable to degrade the proteins to peptides using one or more protease enzymes. Alternatively, or additionally, samples may be processed by separating out certain components prior to being subjected to further handling. Exemplary embodiments of separations were previously discussed under the heading: "Separations". Processing may not be necessary if the analyte is in a form suitable for analysis.

If a determination is to be made as to whether or not a modification of interest causes specific interaction of the analytes of a sample, or sample fraction, with a selected stationary phase (i.e. affinity support), a fraction of each sample or sample fraction (the "specificity control") can be treated with an enzyme (or enzymes) and/or chemical (or chemicals) that removes this modification from analytes of the sample that comprise said modification. Where two or more samples are being simultaneously analyzed, the treated fractions can all be mixed to from a mixture (the "Specificity Control Mixture" or "SCM"). Notwithstanding the foregoing, at least one sample, or fraction thereof, will remain untreated with the enzyme and/or chemical that removes the modification else it will not be possible to compare unmodified and modified analytes by this method.

In order to simplify the analysis, the SCM can be prepared by combining an amount of each of the samples or sample fractions to be examined such that proportionality of signature peaks in the analysis of complex mixtures provide simple to analyze ratio information. For example, if four samples are to be analyzed, one-fifth of each of the four samples can be mixed to form the sample to be reacted with the enzyme or chemical. Accordingly, each of the remaining samples represents $4/5$ths of the original sample and the SCM will be roughly equivalent ($1/5+1/5+1/5+1/5=4/5$ths). As a rule of thumb therefore, the amount to be combined from each sample to form the SCM can be chosen according to the formula: 1/number of samples (or sample fractions)+1=the fraction taken from each sample (or sample fraction) to prepare the SCM. It is to be noted that this is not a limitation as any amount can be withdrawn from the samples for this analysis.

However, following this procedure simplifies the analysis based upon the relative intensities of the peaks observed for the signature ions.

Once the samples to be analyzed have been selected, optionally processed as desired, optionally fractioned (e.g. separated) and optionally had an aliquot withdrawn and treated for specific binding analysis, each sample, or fraction thereof (including the SCM) can be applied to an affinity support and separated into a fraction of analytes that flow through the support and a fraction of analytes that bind to the affinity support. Each sample, or fraction thereof, is applied to a different affinity support. The analytes that bind to the support can be eluted under conditions that differ from those of the flow-through analytes. The analytes that flow through the affinity support can be collected separately as a fraction from those that bind to the affinity support. Processes for performing such separations of modified and unmodified analytes are well known in the art. For example, an IMAC column is well understood to selectively bind phosphopeptides thereby permitting the separation of the phosphopeptides from the associated unmodified version of the peptides.

At this point the fractions of interest can be encoded by reaction of the analytes of each fraction with the isobaric and/or isomeric labeling reagents of a set. Depending on the analysis, certain fractions may not need to be encoded and they can be discarded. Fractions comprising analytes that bind to the affinity support will typically be encoded with a unique labeling reagent of a set of isobaric and/or isomeric labeling reagents. In some embodiments, the fractions comprising analytes that flow through the affinity support will be encoded and in some embodiments these can be discarded.

A discussion of embodiments of such labeling reagents and labeling processes have been previously discussed under the headings: "Labeling Reagents" and "Labeling The Analytes Of A Sample", respectively. Except for the specificity control or the SCM, each of the bound and flow-through sample fractions can be encoded with a different labeling reagent. For the specificity control or SCM, only the fraction containing components that bound to the affinity support will typically be encoded with a unique labeling reagent from the set, although the flow through can be encoded with a unique labeling reagent if desired. Once the labeling is completed, each of the sample fractions (or a sub-fraction thereof) can be mixed together. By mixing all of the samples (or sample fractions) together, a multiplex analysis can be performed in a time and resource efficient manner whereby direct comparisons can be made between the compositions of the different samples (or sample fractions) without the need to apply corrections based upon sample to sample or run to run variation. If absolute quantification is desired, a known amount of calibration standard for analytes of interest can be added to the mixture as previously discussed under the heading: "Relative and Absolute Quantification Of Analytes".

Once mixed, the mixture can be treated chemically or enzymatically to remove the modification of interest from the analytes. Accordingly, all of the analyte components of the mixture are unmodified but are encoded based upon binding properties associated with whether or not they contained the modification of interest at predetermined steps in the process. Accordingly, relevant information about the analyte modifications is present in the mixture after the chemical or enzymatic treatment, although the modifications to all analytes of the mixture have been removed. Stated differently, all analytes at this point should be unmodified but should be encoded in a way that tracks the presence or absence of the modification of the analytes in the original samples that were selected.

After chemical or enzymatic treatment, the sample mixture can optionally be separated prior to mass spectral analysis. Separation can be used to de-complexify the mixture. For example, separation can be used to separate different analytes of the sample mixture, thereby facilitating a simplified and more complete mass spectral analysis. The more complex the sample mixture, the more beneficial will be the performance of one or more steps of separation prior to mass spectral analysis. Where all of the labeling reagents are isobaric, differentially labeled but otherwise identical analytes will not be distinguishable by the separations technique. Some or all of the fractions so obtained can be analyzed in the mass spectrometer to thereby gather as much information about the component analytes of each of the original samples as is possible. Exemplary analysis by a mass spectrometer has been previously discussed under the headings: "Mass Spectrometers/Mass Spectrometry", "Fragmentation By Dissociative Energy Levels" and "Analyte Determination By Computer Assisted Database Analysis".

For example, the sample mixture (or fractions thereof) can be analyzed by mass spectral analysis, including MS/MS analysis. In the MS/MS analysis, signature ions can be determined for different labeled analytes of the sample mixture, wherein each signature ion correlates with the unique labeling reagent of an encoded sample fraction and the peak intensity of the signature ion correlates with the relative quantity of that analyte in the sample mixture. From the relative intensity information of signature ions for each analyte, it is possible to determine relative amounts of modified and unmodified analyte in each of the original samples, and optionally (where a specificity control or SCM was prepared), whether or not the analyte exhibited specific or non-specific binding to the affinity support. Daughter fragment ion analysis can further be used to determine the analytes (e.g. peptides) as well as precursor molecules (e.g. proteins) where the analytes identified in the mass analysis were obtained from precursor molecules.

Specifically, if a specificity control or SCM were separately applied to an affinity support and at least the fraction of analytes that bind to the affinity support were separately labeled with a unique labeling reagent, it is possible to determine whether or not analytes comprising the modification specifically interact with the affinity support. This information is possible by determining whether or not the signature ion for the unique labeling reagent associated with specificity control or SCM is observed. If the signature ion is observed, the interaction with the affinity support is non-specific. If the signature ion for the specificity control or SCM is not observed, the interaction with the affinity support is specific.

As discussed under the heading, "Analyte Determination By Computer Assisted Database Analysis", from the daughter ion analysis it is possible to identify one or more of the analytes in the mixture. If the analytes are obtained from precursor molecules it may be possible to obtain the identity of one or more of the precursor molecules. For example, if the daughter ion analysis identifies one or more peptide analytes in the sample, it may be possible to identify one or more protein analytes in the sample where the proteins were digested to produce the peptide analytes. The following discussion and examples are illustrative of how this analysis can be performed.

Furthermore, because the samples and sample fractions have been encoded, the relative intensity of the signature ions in the mixture can be correlated with the relative amount of modified and unmodified versions of the identified analyte in the mixture that is analyzed. This information relates back to the original samples such that it is possible to determine the relative and/or absolute amount of a particular modified analyte and its corresponding unmodified analyte in each of the original samples. Where the analytes are obtained from precursor molecules, it is possible to determine the relative and/or absolute amount of a particular modified precursor molecule (itself an analyte) and its corresponding unmodified precursor molecule (itself an analyte) in each of the original samples. The following discussion and examples are illustrative of how this analysis can be performed.

6. ILLUSTRATIVE EMBODIMENTS

The discussions set forth below focus on determining the relative and/or absolute quanitation of phosphopeptides in one or more samples, or fractions thereof. Phosphopeptides can be generated in a cell as a consequence of a post-translational modification (PTM). The presence of the phosphate group of the phosphopeptides is therefore a characteristic of interest that can be determined by embodiments of this invention. However, the specific processes discussed below can be adapted for determining any modification or other characteristic of interest of an analyte, where the modification (or characteristic associated with a modification) can be removed by enzymatic or chemical means to thereby generate the native (unmodified) analyte. The processes discussed below could also include, but is not limited to, affinity (or antibody) pull-downs of specific proteins or protein complexes where the encoding could be used to distinguish specific from non-specific interactions. Viewed broadly, the tagging could be used to encode samples in any situation where you wish to reliably discriminate between experimental and control outcomes. With multiplexing, this could encompass experiment and multiple controls. The following examples are therefore intended to be illustrative of the invention and not limiting in any way.

The identification of post-translationally modified cellular analytes in complex mixtures can be problematic. This is particularly true for phosphopeptides. Detection limits for phosphopeptides in a mass spectrometer can be significantly reduced because they are often present in low molar abundance (often less than 10%) when compared to corresponding native (non-phosphorylated) peptide. In addition, the strongly negative phosphate group can cause ion suppression in both electrospray (ES) and matrix assisted laser desorption (MALDI) mass spectral analysis, thereby reducing the observed ion intensity. It is therefore not surprising that phosphopeptides are rarely successfully identified in many proteome-scale projects of high sample complexity, where the relatively weak phosphopeptide signals are often masked by other ions or suppressed by other sample components. Although sample complexity can be reduced by affinity chromatography or the application of pure MS techniques (e.g. as precursor or neutral-loss scanning mode), the low molar abundance and poor ionization efficiency of the phosphorylated peptides mitigate against detection in complex peptide samples.

Accordingly, in some embodiments, this invention pertains to methods, mixtures and/or kits suitable for the analysis of post-translational modifications (PTMs) of cellular analytes. All types of post-translational modifications can be determined. For example, the post-translational modification can comprise phosphorylation, glycosylation or metal modification of a cellular analyte. The cellular analyte can be any cellular constituent, such as a peptide, protein, antibody (including antibody fragments) nucleic acid, carbohydrate, lipid or steroid.

Illustrative methods are disclosed below. Embodiments of mixtures include the sample mixture wherein analytes are encoded with labeling reagents that identify the sample fraction from which they originate. Embodiments of kits include kits suitable to perform the disclosed methods as well as those that can be used to produce the disclosed sample mixtures. A kit could for example, comprise a set of isobaric labeling reagents and an affinity support suitable for separation modified from unmodified analytes of interest.

Figure 1B:
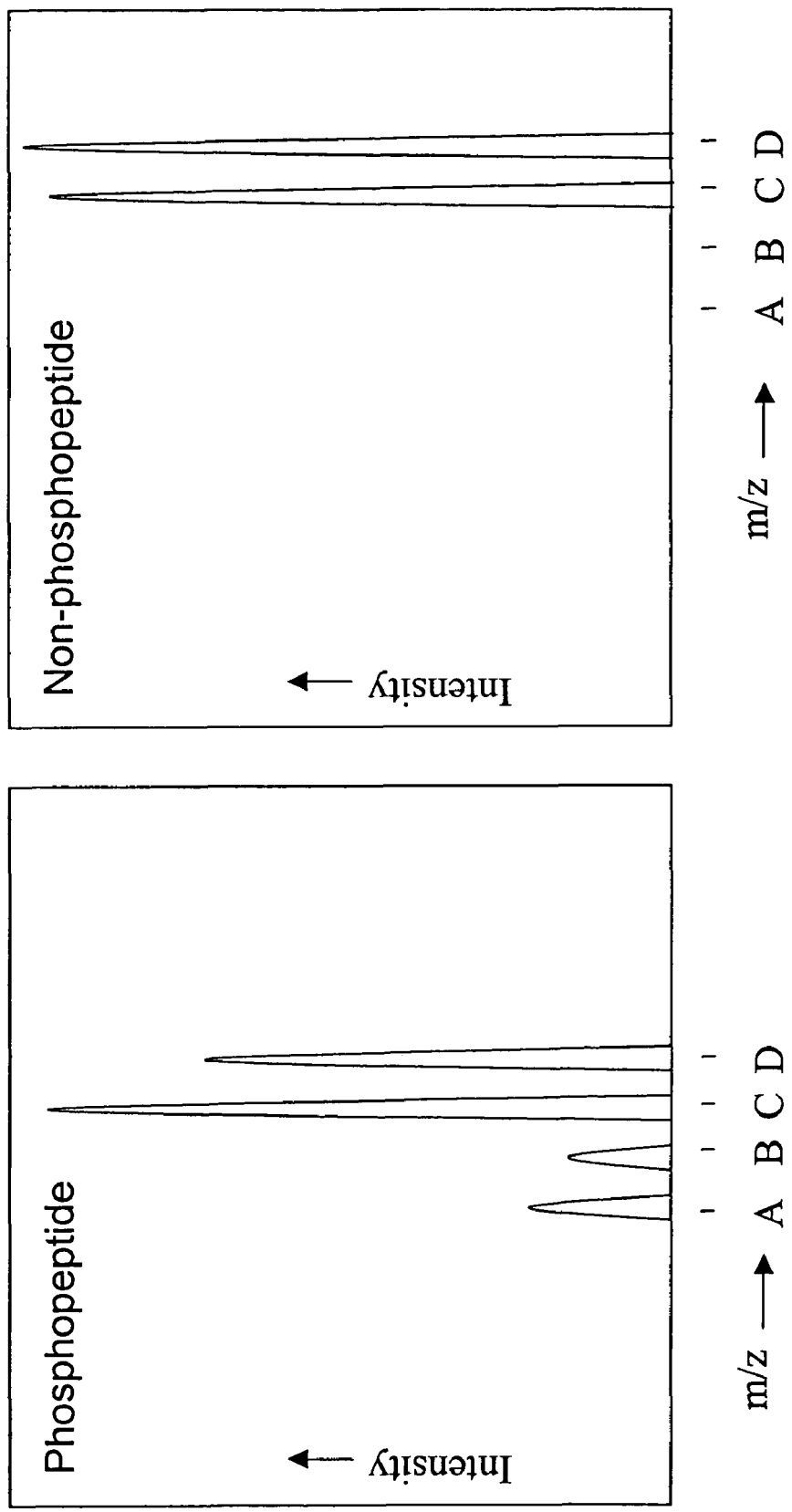

Determination of Analyte Modifications Based Upon Characteristic Affinity Properties With reference to FIG. 1a, 1b and Example 1, a description of one mode of determining post-translational modifications, or other characteristic property of an analyte, is illustrated. According to the illustration of FIG. 1a, two samples (i.e. Sample 1 and Sample 2) comprising an analyte such as protein (e.g. from a cell lysate) can be processed by treatment with a proteolytic enzyme (e.g. trypsin) to thereby digest component proteins. The digest can comprise both unmodified and modified peptides (e.g. phosphor glyco-, or metallopeptides). For each modified peptide, there can be a correlating native (unmodified) peptide present in greater or lesser abundance as compared with the modified peptide.

Each sample of digested material can be chromatographically separated to thereby separate the modified peptides from the unmodified peptides. For example, an immobilized-metal affinity chromatography (IMAC) column is suited for, and is known to facilitate, the immobilization of phosphopeptides. The stationary phase and chromatographic conditions can be optimized for other types of modifications. Basically, the separation can be carried out so that bound components, that are likely to possess the property of interest (e.g. be a phosphopeptide), can be separated from the other components of the sample. The bound components can be eluted separately from components that flow through the stationary phase so that both the bound and unbound (flow-through) components of each sample are collected separately. Accordingly, for a two-sample system, there can be four collected sample fractions. The number of fractions according to this illustration will be two times the number of samples to be compared.

As illustrated in FIG. 1a, each of the four sample fractions can be reacted with a different isobaric or isomeric labeling reagent of a set of labeling reagents. For example, each labeling reagent could be designated as Reagent A, Reagent B, Reagent C and Reagent D, wherein, for example, the reagents generate fragment ions of 114, 115, 116 and 117 amu, respectively when subjected to MS/MS analysis. At this point, the labeling reagents can react with the modified and unmodified peptides (analytes) of each of the four fractions.

As illustrated in FIG. 1a, once each of the four fractions is labeled with one of the four different isobaric and/or isomeric labeling reagents, they (or a fraction thereof) can be mixed to form a sample mixture (i.e. "MIX" in the Figure). According to FIG. 1a, said mixture can contain both modified and unmodified peptides from both Samples 1 and 2, wherein those peptides from Sample 1 will be labeled (encoded) with Reagent A (114) or Reagent C (116) and those peptides from Sample 2 will be labeled (encoded) with Reagent B (115) or Reagent D (117). An exemplary set of isobaric labeling reagents that produce signature ions of mass/charge 114, 115, 116 and 117 are illustrated in FIG. 4.

The sample mixture can then be treated with an enzyme (or enzymes) or chemical (or chemicals) to remove the modification from the analytes of the sample mixture. For example, the phospho-group of a phosphopeptide can be removed by treatment with one or more phosphatase enzymes (e.g. serine (S), threonine (T) or tyrosine (Y) phosphatates). After treatment, what were previously modified and unmodified versions of the same analyte are now all unmodified. However, all of the peptide analytes to be determined comprise a label that encodes the sample fraction, as well as the sample (i.e. Sample 1 or Sample 2), from which they originated. If the labels are isobaric, despite the differing labels, identical analytes (e.g. peptides) can be chemically and structurally indistinguishable (except for the differing distribution of heavy atom isotopes) especially in any separations process. Thus, subsequent separation, such as multidimensional liquid chromatography (LC) can optionally be performed. This is not a problem since fractions of the sample mixture (created by the separations process) will comprise each labeled analyte in proportion to its quantity or concentration in the sample mixture.

After the treatment with the chemical or enzyme to remove the modification (or characteristic of interest associated with a removable modification) and optional separation, the sample mixture, or a fraction thereof, can be analyzed in a mass spectrometer. As discussed above, in MS/MS mode, the daughter ions of each analyte can be used to determine peptides and/or protein of the sample by selection of ions from the MS analysis. Furthermore, for each analyte peptide, the relative quantity of that peptide in each of the four fractions used to produce the sample mixture can be determined based upon each signature ion peak of the reporter of each labeling reagent.

With reference to FIG. 1b, the pattern observed for the signature ions can be used to determine the results of the samples applied to the workflow illustrated by FIG. 1a. As can be seen by analysis of FIG. 1b, if an analyte exhibits affinity for the IMAC column (i.e. is a phosphopeptide), it will be immobilized on the column and be labeled with Reagent A or Reagent B. Thus, if the analyte binds to the affinity support, signature ions for Reagent A and Reagent B will be observed in the MS/MS analysis. If no binding to the affinity column occurs, signature ions for only Reagents C and D will be observed in the MS/MS analysis. It should be noted that the peak intensity for the signature ion for each of the labeling reagents is in proportion to the amount of the analyte in the sample mixture. Based upon knowledge of the amount (e.g. volume) of each sample fraction added to form the sample mixture, it is possible to back calculate the amount (typically reported in terms of concentration or quantity) of the analyte in each of the sample fractions as well as in each of Sample 1 and Sample 2.

If absolute quantification of the analyte is desired, it is possible to spike the sample mixture with a known amount of the calibration standard analyte differentially labeled with an isobaric or isomeric label of the set of labeling reagents. In this way the relative amounts of signature ions for the analyte can be compared relative to the known amount of the calibration standard. By relation to the quantity of calibration standard, the absolute amount of the analyte in each of the samples used to form the sample mixture can be determined based upon the relative intensity of the signature ions.

A caveat to the foregoing method is whether or not the binding of the analyte to the stationary phase can be correlated with the presence of the modification sought to be determined. That is because the binding of an analyte to a support can be either specific or non-specific. The following example illustrates how to determine, using the isobaric and/or isomeric labeling reagents, whether or not an observed affinity of the analyte for the support is specifically caused by the modification (or the characteristic of interest).

Determination of the Specificity of Affinity Binding Properties

Figure 2A:
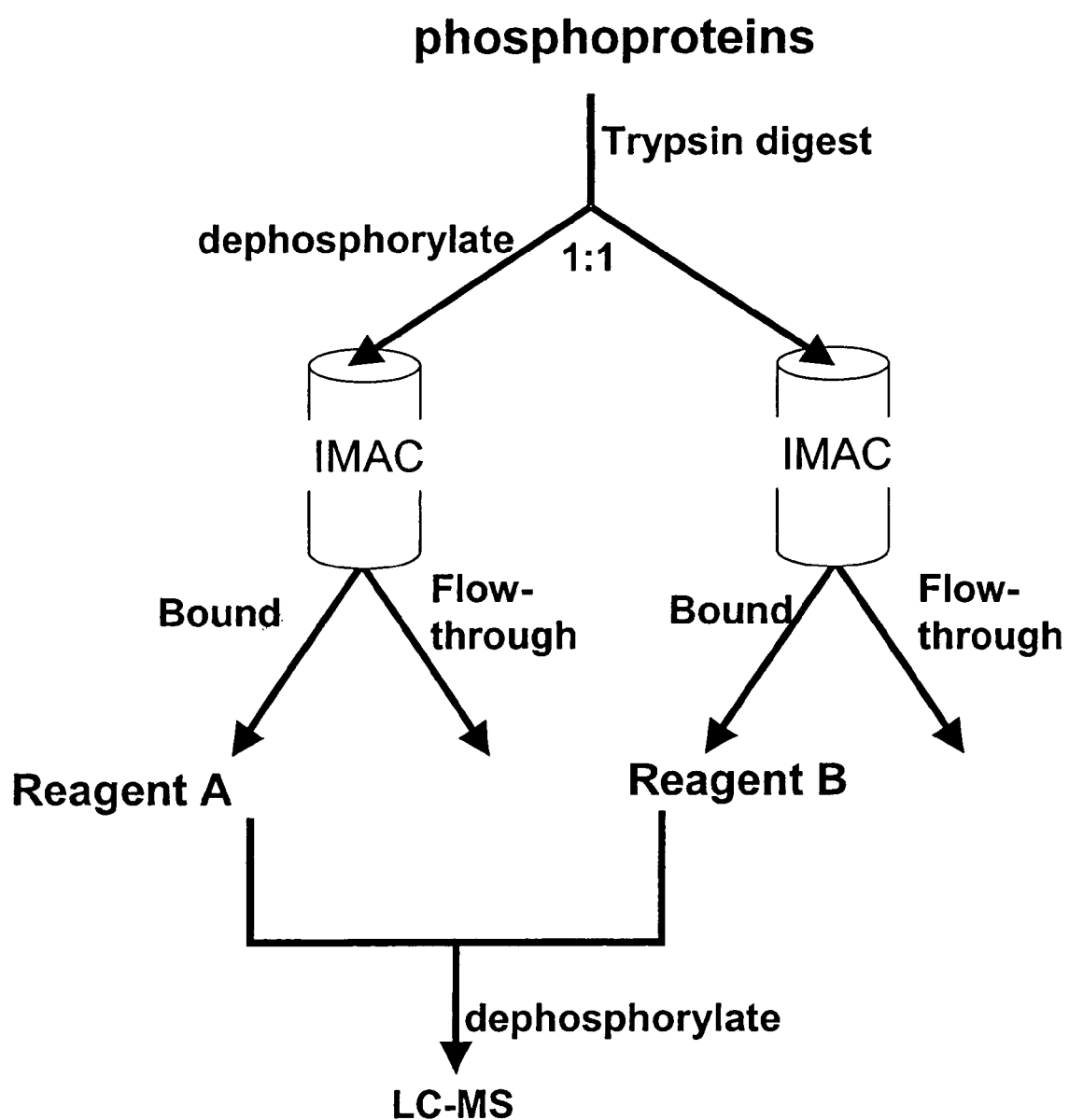
FIG. 2a illustrates the workflow for one embodiment of the analysis of a sample for the presence of phosphopeptides, wherein specific and non-specific binding of the analyte to the affinity support can be determined.
Figure 2B:
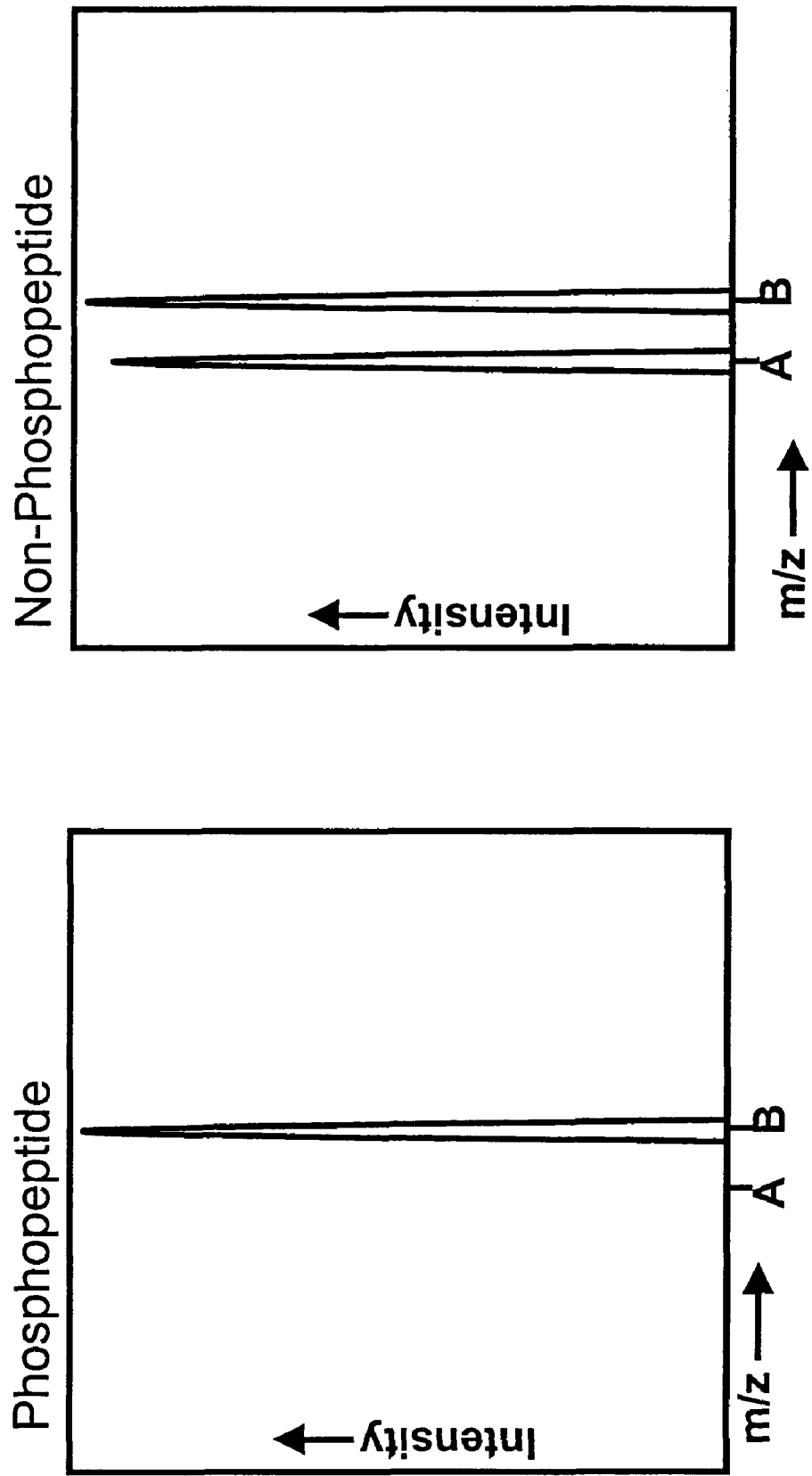

With reference to FIG. 2a, 2b and Example 2, illustrated is a description of one mode of determining whether or not a characteristic property of an analyte results in specific binding to a stationary phase. According to the method, a sample comprising an analyte or analytes (such as a protein from a cell lysate) can be processed by treatment with a proteolytic enzyme (e.g. trypsin) to thereby digest components of the sample. For protein, the digest can comprise both unmodified and modified peptides (e.g. phosphor glyco-, or metallopeptides). For each modified peptide, there can be a correlating native (unmodified) peptide present in greater or lesser abundance as compared with the modified peptide.

With reference to FIG. 2a, the digested sample, or a fraction thereof, can be split into two sample fractions. Typically the two sample fractions will be of equal volume, but this is not a requirement so long as the relative amounts are known. One of the two sample fractions can be chemically or enzymatically treated to remove the modification that is to be examined for specific or non-specific interaction with a particular stationary phase. The other of the two sample fractions can be taken on without further sample processing.

Each of the two sample fractions is then applied to the stationary phase of interest. For example, an immobilized-metal affinity chromatography (IMAC) column is suited for, and is known to facilitate, the immobilization of phosphopeptides. The stationary phase and chromatographic conditions can be optimized for other types of modifications. Basically, the separation can be carried out so that bound components, that are likely to possess the property of interest (e.g. be a phosphopeptide), can be separated from the other components of the sample. The bound components can be eluted separately from components that flow through the stationary phase so that both the bound an unbound (flow-through) components are collected separately.

As illustrated in FIG. 2a, only the fractions containing components that may have bound to the stationary phase need be reacted with a different isobaric or isomeric labeling reagent of a set of labeling reagents. Although the "flow-through" fractions can be labeled, and analyzed, this is not essential for determining whether or not the interactions of the components with the stationary phase are specific or non-specific.

As illustrated in FIG. 2a, once each of the fractions to be labeled is indeed labeled with one of the different isobaric and/or isomeric labeling reagents, they (or a fraction thereof) can be mixed to form a sample mixture. Said sample mixture can contain both modified and unmodified peptides. According to FIG. 2a, the sample mixture can then be treated with an enzyme or chemical to remove the modification from the analyte. For example, the phospho-group of a phosphopeptide can be removed by treatment with one or more phosphatase enzymes. After treatment, what were previously modified and unmodified versions of the same analyte are now all unmodified.

However, all of the analytes to be determined comprise a label that encodes the sample fraction, and possibly the sample (i.e. Sample 1 or Sample 2), from which they originated. If the labels are isobaric, despite the differing labels, identical analytes (e.g. peptides) can be chemically and structurally indistinguishable (except for the differing distribution of heavy atom isotopes) especially in any separations process. Thus, subsequent separation, such as multidimensional liquid chromatography (LC) can optionally be performed. This is not a problem since fractions of the sample mixture (created by the separations process) will comprise each labeled analyte in proportion to its quantity or concentration in the sample mixture.

After the treatment with the chemical or enzyme to remove the modification (or characteristic of interest associated with a removable modification) and optional separation, the sample mixture, or a fraction thereof, can be analyzed in a mass spectrometer. As discussed above, in MS/MS mode, the daughter ions of each analyte can be used to determine peptides and/or protein of the sample by selection of ions from the MS analysis. Furthermore, for each analyte peptide, the relative quantity of that peptide in each of the fractions used to produce the sample mixture can be determined based upon each signature ion peak of the reporter of each labeling reagent.

With reference to FIG. 2b, the pattern observed for the signature ions can be used to determine the results of the samples applied to the workflow illustrated by FIG. 2a. As can be seen by analysis of FIG. 2b, if an analyte exhibits affinity for the IMAC column (i.e. is a phosphopeptide), it can be immobilized on the column, be eluted from the column and be labeled with Reagent A or Reagent B. With reference to FIG. 2b, if the analyte binds specifically to the stationary phase, there should be little or no signature peak observed for labeling reagent A since the removal of the modification prior to contact with the stationary phase should eliminate specific binding of the analytes to the stationary phase. However, if the interaction with the stationary phase is non-specific, at least some signature peak will be observed for labeling reagent A since removal of the modification will have little or no effect on the interaction of the modification with the stationary phase.

It should be noted that the peak intensity for the signature ion for each of the labeling reagents is in proportion to the amount of the analyte in the sample mixture. Based upon knowledge of the amount (e.g. volume or concentration) of each sample fraction added to form the sample mixture, it is possible to back calculate the amount (typically reported in terms of concentration or quantity) of the analyte in each of the sample fractions, and if appropriate in each of the samples used in an assay.

If absolute quantification of the analyte is desired, it is possible to spike the sample mixture with a known amount of the calibration standard analyte differentially labeled with an isobaric or isomeric label of the set of labeling reagents. In this way the relative amounts of signature ions for the analyte can be compared relative to the known amount of the calibration standard. By relation to the quantity of calibration standard, the absolute amount of the analyte in each of the samples used to form the sample mixture can be determined based upon the relative intensity of the signature ions.

Figure 3A:
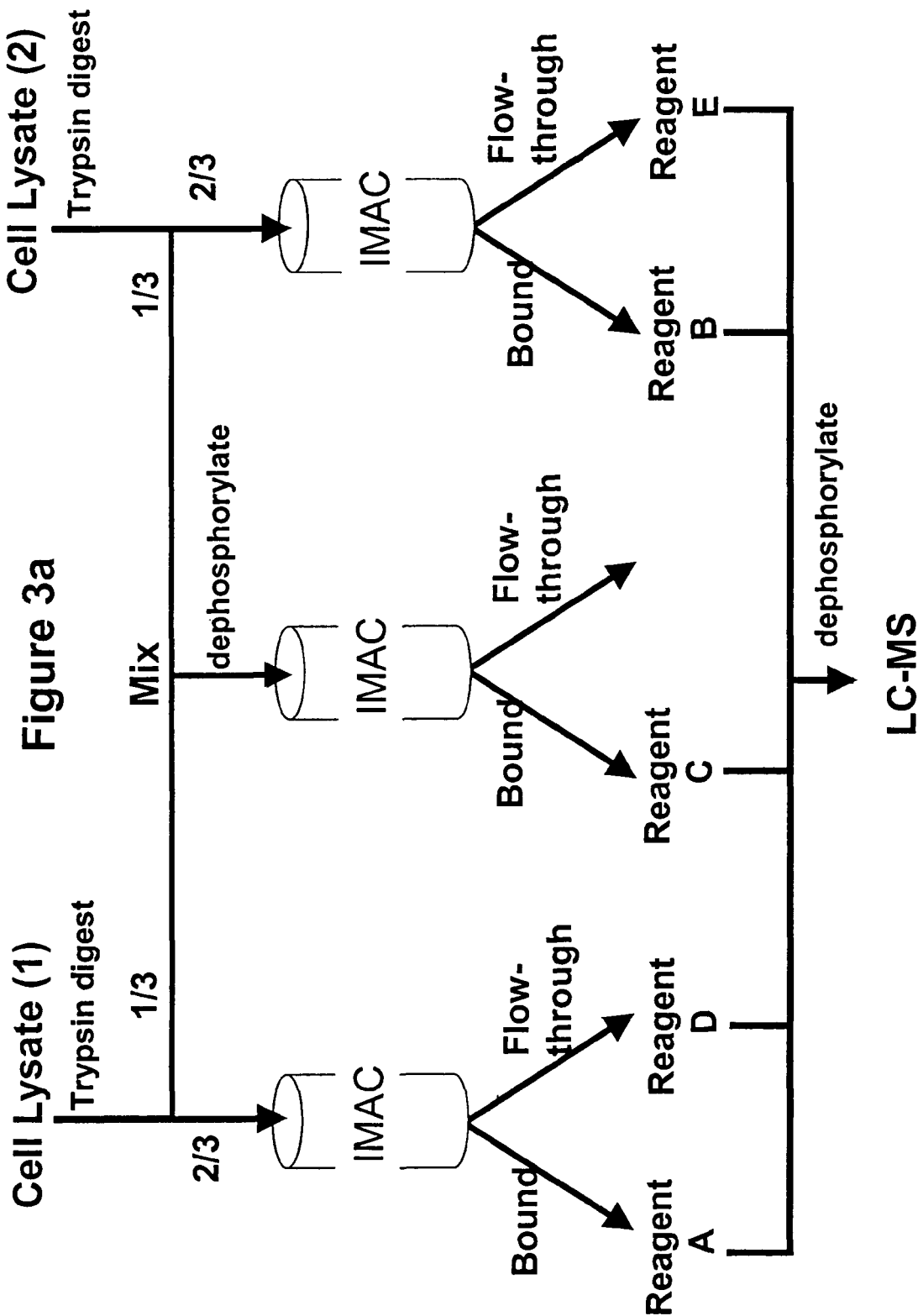
FIG. 3a illustrates the workflow for one embodiment of the analysis of Sample 1 and Sample 2 for the presence of phosphopeptides wherein specific and non-specific binding of the analyte to the affinity support can be simultaneously determined.
Figure 3B:
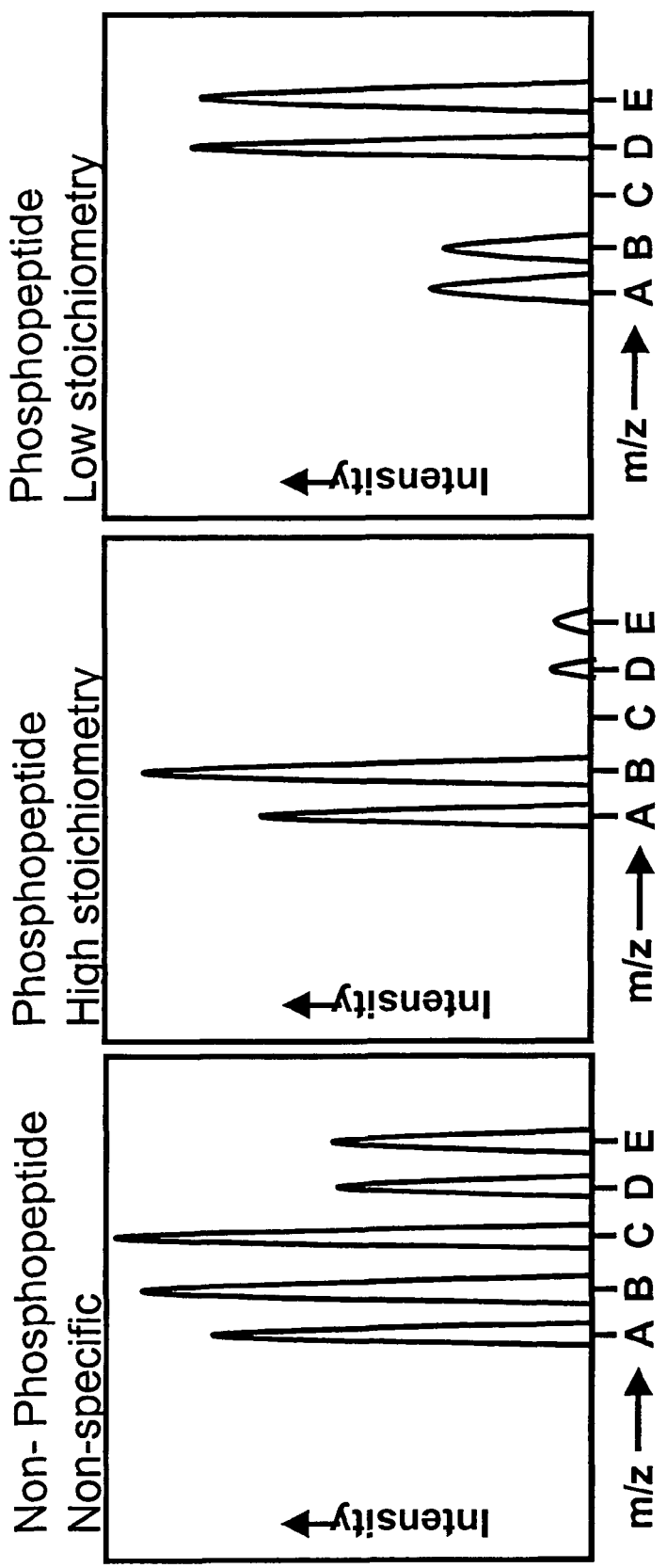

Determination of Analyte Modifications and the Specificity of Binding Affinity of the Modification to a Support With reference to FIG. 3a, 3b and Example 3, illustrated is a description of one mode of determining both the presence of a modification in sample components and whether or not the modification results in specific binding to a stationary phase. According to the method, two samples comprising an analyte or analytes (such as a protein from a cell lysate) can be processed by treatment with a proteolytic enzyme (e.g. trypsin) to thereby digest components of the sample. For protein, the digest can comprise both unmodified and modified peptides (e.g. phosphor glyco-, or metallopeptides). For each modified peptide, there can be a correlating native (unmodified) peptide present in greater or lesser abundance as compared with the modified peptide.

With reference to FIG. 3a, each digested sample, or a fraction thereof, can be split into two sample fractions. According to the illustration each sample can be divided into aliquots of ⅔ and ⅓, but this is not a requirement so long as the relative amounts are known. According to the illustration, each of the ⅓ sample fractions can be combined (⅓+⅓=⅔) and chemically or enzymatically treated to remove the modification that is to be examined for specific or non-specific interaction with a particular stationary phase. By combining the two fractions of ⅓, all of the amounts of the samples applied to the IMAC columns are identical (i.e. ⅔). This approach can simplify the relative quantitation analysis based upon reporter signal analysis). The remaining ⅔ of each sample can be taken on without further sample processing.

Each of the three sample fractions can then applied to the stationary phase of interest. For example, an immobilized-metal affinity chromatography (IMAC) column is suited for, and is known to facilitate, the immobilization of phosphopeptides. The stationary phase and chromatographic conditions can be optimized for other types of modifications. Basically, the separation can be carried out so that bound components, that are likely to possess the property of interest (e.g. be a phosphopeptide), can be separated from the other components of the sample. The bound components can be eluted separately from components that flow through the stationary phase so that both the bound an unbound (flow-through) components of each sample are collected separately.

As illustrated in FIG. 3a, only the fractions containing components that may have bound to the stationary phase need be reacted with an isobaric or isomeric labeling reagent of a set of labeling reagents for the sample treated enzymatically or chemically to remove the modification of interest (i.e. Reagent C in the illustration). For the samples that were not treated to remove the modification, both the bound and flow-through fractions should each be labeled with a different isobaric and/or isomeric labeling reagent of a set of reagents. As illustrated, each labeling reagent could be designated as Reagent A, Reagent B, Reagent C, Reagent D and Reagent E, wherein, for example, the reagents generate fragment ions of 113, 114, 115, 116 and 117 amu, respectively when subjected to MS/MS analysis. At this point, the labeling reagents can react with the modified and unmodified peptides (analytes) of each of the two or four fractions, as desired to thereby encode the components of each fraction.

As illustrated in FIG. 3a, once each of the fractions to be labeled is indeed labeled with one of the different isobaric and/or isomeric labeling reagents, they (or a fraction thereof) can be mixed to form a sample mixture. Said mixture can contain both modified and unmodified analytes (e.g. peptides). According to FIG. 3a, the sample mixture can then be treated with an enzyme or chemical to remove the modification from the analyte. For example, the phospho-group of a phosphopeptide can be dephosphorylated by treatment with one or more phosphatase enzymes. After treatment, what were previously modified and unmodified versions of the same analyte are now all unmodified.

However, all of the analytes to be determined comprise a label that encodes the sample fraction, and possibly the sample from which they originated. If the labels are isobaric, despite the differing labels, identical analytes (e.g. peptides) can be chemically and structurally indistinguishable (except for the differing distribution of heavy atom isotopes) especially in any separations process. Thus, subsequent separation, such as multidimensional liquid chromatography (LC) can optionally be performed. This is not a problem since fractions of the sample mixture (created by the separations process) will comprise each labeled analyte in proportion to its quantity or concentration in the sample mixture.

After the treatment with the chemical or enzyme to remove the modification (or characteristic of interest associated with a removable modification) and optional separation, the sample mixture, or a fraction thereof, can be analyzed in a mass spectrometer. As discussed above, in MS/MS mode, the daughter ions of each analyte can be used to determine peptides and/or protein of the sample by selection of ions from the MS analysis. Furthermore, for each analyte (e.g. peptide), the relative quantity of that peptide in each of the fractions used to produce the sample mixture can be determined based upon each signature ion peak of the reporter of each labeling reagent.

With reference to FIG. 3b, the pattern observed for the signature ions can be used to determine the results of the samples applied to the workflow illustrated by FIG. 3a. As can be seen by analysis of FIG. 3b, for analytes that exhibit affinity for, and therefore bind to, the IMAC column (i.e. is a phosphopeptide), these can be labeled with reagents A and B. Accordingly, the intensity of peaks for reagents A and B indicate the amount of modified analyte (e.g. phosphopeptide) in the original samples. Similarly, the amount of unmodified analyte in the original samples can be determined from the fractions labeled with reagents D and E. Accordingly, ratios can be determined for the amount of modified and unmodified analyte in each of the original samples based upon the ratios of reporters for reagents A, B, D and E in the MS/MS analysis.

With reference to FIG. 3b, if the analyte binds specifically to the stationary phase, there should be little or no signature peak observed for labeling reagent C since the removal of the modification prior to contact with the stationary phase should eliminate specific binding of the analytes to the stationary phase. However, if the interaction with the stationary phase is non-specific, at least some signature peak will be observed for labeling reagent C since removal of the modification will have little or no effect on the interaction of the modification with the stationary phase. Accordingly, a determination of whether or not that modification resulted in a specific interaction with the stationary phase can also be determined by this workflow.

It should be noted that because of the way the samples were processed, the peak intensity for the signature ion for each of the labeling reagents should in proportion to the amount of the analyte in the sample mixture. Based upon knowledge of the amount (e.g. volume or concentration) of each sample fraction added to form the sample mixture, it is possible to back calculate the amount (typically reported in terms of concentration or quantity) of the analyte in each of the sample fractions, and if appropriate in each of the samples used in an assay.

If absolute quantification of the analyte is desired, it is possible to spike the sample mixture with a known amount of the calibration standard analyte differentially labeled with an isobaric or isomeric label of the set of labeling reagents. In this way the relative amounts of signature ions for the analyte can be compared relative to the known amount of the calibration standard. By relation to the quantity of calibration standard, the absolute amount of the analyte in each of the samples used to form the sample mixture can be determined based upon the relative intensity of the signature ions.

General Comments to the Various Disclosed Embodiments

In each of the foregoing disclosed embodiments, absolute quantitation of analytes can be determined, based upon the relative quantitation, if a standard for the analyte is added to the sample mixture.

Although the present invention has been disclosed as set forth above, it should be understood that various changes, substitutions, and alterations can be made herein. Moreover, other examples are readily ascertainable by one skilled in the art and can be made without departing from the spirit and scope of the present invention as defined by the following claims.

EXAMPLES

Example 1

Prophetic

Simple Multiplex Analysis of PTMs Using Affinity Chromatography (FIGS. 1a & 1b)

This example is illustrated with reference to FIGS. 1a and 1b. With reference to FIG. 1a, Sample 1 and Sample 2 are total protein lysates from cells or tissues selected for comparison. Non-limiting examples of this would be normal versus diseased cells or tissues, cells or tissues treated (or not) with drugs or other small molecules and samples of biological fluid (serum, urine, spinal fluid) taken from the same or different patients during the course of disease progression or disease treatment.

The protein lysates are separately digested with a protease (e.g. trypsin) and the resulting peptides subjected to affinity chromatography with an IMAC column to thereby selectively bind those peptides containing a phosphate group. The flow-through fractions (e.g. non-phosphorylated peptides) are collected and then the bound (phosphorylated) peptides are selectively desorbed and collected from each IMAC column.

Each of the four pools of peptides (bound and flow-through fractions from the 2 IMAC columns) is individually reacted with one member of a 4-plex set of the isobaric labeling reagents (i.e. reagents A, B, C and D). The four pools are then mixed together and treated with a cocktail of serine, threonine and tyrosine (S, T and Y) phosphatases to remove all bound phosphate groups. The mixture of peptides is then chromatographically separated by 1D, 2D or multi-dimensional LC and the peptides analyzed by MS, fragmented by dissociate energy and selected ions analyzed by MS/MS analysis. The isobaric labeling reagents are chemically identical, so there is no chromatographic separation of corresponding peptides, and identical peptides from the four pools are isobaric in mass. The strategy at this point is to collect as much data on as many peptides as possible within time or sample-limiting constraints. Examination of the collected MS/MS collision spectra can now be used to quantify relative peptide (and therefore protein) abundance between Samples 1 and 2, and at the same time allow for the specific identification (based upon daughter fragment ion analysis) and quantitation of phosphopeptides (based upon relative signature ion analysis of the reporters) within the mixture.

FIG. 1b illustrates a theoretical pattern of the 'signature' ion peaks of the isobaric labeling reagents following CID of individual peptides. In this example, the signature ion peaks (i.e. labeling reagents A, B, C and D) are one Dalton apart, but this spacing may be 2, 3, 4 or more apart. For any given peptide, the following information can be derived by examination of the signature-ion region of the CID spectrum:

1) Only peptides that were phosphorylated in the initial samples will have signature-ion for reagent A and/or B. The absence of peaks A and B indicates that the peptides were not phosphorylated in the original samples.
2) If present (phosphopeptides only) the relative intensity ratio of peak A to peak B can be used to determine the relative phosphorylation state of the peptide in Sample 1 as compared with Sample 2 (equal intensity means no change; this statement assumes similar treatments for Samples 1 and 2, including similar amounts of samples, or sample fractions, were applied to the IMAC columns)

3) The relative intensities of peaks C and D can be used to determine the relative concentration of a given peptide in Sample 1 and Sample 2 (all peptides; this statement assumes similar treatments for Samples 1 and 2, including similar amounts of samples, or sample fractions, were applied to the IMAC columns).

4) The relative ratios of peak A to peak C and peak B to peak D can be used to determine the relative stoichiometry of phosphorylation of any given peptide in Sample 1 and Sample 2 (e.g. 5%, 10%, 25%; this statement assumes similar treatments for Samples 1 and 2, including similar amounts of samples, or sample fractions, were applied to the IMAC columns).

The following are generally observed advantages of this method:

1) The method permits simultaneous identification and quantitation of phosphopeptides in complex sample mixtures. It is very efficient in terms of time and sample consumption as this data is collected in parallel with data relating to relative peptide concentration of all (non-phosphorylated) peptides as well.

2) Treatment with the phosphatases has several beneficial consequences. Removal of the phosphate group reduces overall sample complexity as all peptides are reduced to the same, native form. This is good for both chromatographic and MS resolution. Removal of the phosphate group increases the ionization efficiency (and thus signal intensity) of the peptides, increasing detection sensitivity. In effect, we have added the signal from a minor (5-10%) phosphorylated form of any given peptide into the signal from the major component of the native peptide. The identification and quantitation information is now present in the same, single set of CID spectra.

3) The method improves ability to identify phosphopeptides by CID and searching sequence databases with programs such as SEQUEST and MASCOT. The described procedure has the effect of adding all the low-yield, poorly ionizable phosphopeptide signals into the same major signal component of the unmodified, parent peptide.

4) The method suits peptide-based proteomic workflows. For a little additional sample preparation (IMAC columns) the data collected from a single multi-dimensional LC experiment can be analyzed to identify and quantify any given peptide between theoretical Samples 1 and 2 and simultaneously identify and quantify any phosphopeptides that were present.

One caveat to this workflow approach is that no determination can be made as to whether or not the binding of the analyte to the stationary phase was specific or non-specific. That is to say, just because the analyte bound to the IMAC column, it may not be a phosphopeptide, as some non-phosphorylated peptides are known to bind to IMAC columns. The following example describes how to determine whether or not an analyte exhibits specific or non-specific interactions with the stationary phase.

Example 2

Prophetic

Discrimination Between Specific and Non-Specific Affinity Binding (FIG. 2a, 2b)

A sample of phosphoprotein(s) is digested with a protease (e.g. trypsin) and the digested pool of peptides is split into two fractions (see FIG. 2a). It is not important that the fractions be of equal volume, so long as any difference in volume is known and can be correlated with the peak intensity of the reporter in the MS/MS analysis. One fraction is treated enzymatically with a phosphatase (or chemically) to remove all covalently bound phosphate of the components of the sample fraction. This fraction is thus intended to act as the control sample. The two samples are then each subjected to chromatographic separation using an IMAC column to selectively bind those peptides containing a phosphate group. The flow-through (non-phosphorylated) peptides are collected, and then the bound (potentially phosphorylated or non-specific binding) peptides are selectively desorbed and collected from each IMAC column. This produces potentially four separate sample fractions (see FIG. 2a).

Each of these selectively desorbed (bound) fractions is individually reacted with one member of a isobaric reagent set (A or B), provided that sample fractions derived from a particular IMAC column are both reacted with the same isobaric label. The labeled peptide pools are then mixed and treated enzymatically (e.g. with phosphatases) or chemically to remove bound phosphate. All peptides have now been converted to their native, non-phosphorylated forms.

The mixture of peptides is then subjected to chromatographic separation (e.g. 1D, 2D or multi-dimensional LC) and the peptides are analyzed by MS and tandem MS/MS. The isobaric reagent tags are chemically identical so there is no chromatographic separation of labeled peptides, and identical peptides from the two pools are isobaric in mass (MS). Following MS/MS, examination of the signature ion peaks resulting from CID of the isobarically tagged peptides will permit discrimination of specific or non-specific binding of peptides to the IMAC affinity support, and thus discrimination of true phosphopeptide binding as compared to non-specific binding.

With reference to FIG. 2b, a theoretical pattern of signature ion peaks from the isobaric reagent tags following CID of individual peptides is illustrated. In this experiment, reagent A was used to label the control sample that was de-phosphorylated prior to immobilization to the IMAC column. Thus, true-binding phosphopeptides should display essentially only tag B since there should be no modified analyte remaining in the material applied to the IMAC column. However peptides binding non-specifically to the IMAC support should display signals from both reagents A and B since binding is not dependent upon the presence of absence of the phosphate modification. The labeling reagent 'A' is thus being used as a 'flag' signal, indicating that this peptide is likely to be a non-specific binder, and should not be considered as a phosphopeptide. It should be noted that the ratio of peaks for labeling reagents A and B should be approximately in proportion to the ratio of the amount of the two fractions applied to the IMAC columns if the phosphate modification does not have any affinity for the stationary phase.

Example 3

Prophetic

Analysis of the Binding Affinity of Multiple Analytes (FIGS. 3a & 3b)

This concept of using one of the members of the isobaric reagent set to act as a 'flag' to differentiate true from non-specific phosphorylation can be extended from a single phosphoprotein, as described above, to a full proteome analysis (FIGS. 3a, 3b).

Cell lysates 1 and 2 (FIG. 3a) can be total protein lysates from cells or tissues selected for comparison. Non-limiting examples of this type could be normal versus diseased tissues, cells treated (or not) with drugs or other small molecules and/or samples of biological fluid (serum, urine, spinal fluid) taken from the same or different patients during the course of disease progression or disease treatment.

The protein lysates are separately digested with a protease (e.g. trypsin). The digested lysates are then split according to the ratios shown in FIG. 3a (⅔ and ⅓ aliquots from each lysate). The ⅔ aliquots are subjected to IMAC to selectively bind those peptides containing a phosphate group. The flow-through (putative non-phosphorylated) peptides are collected, and then the bound (putative phosphorylated or non-specific binding) peptides are selectively desorbed and collected. The ⅓ fractions from each of cell lysates 1 and 2 are mixed, treated chemically or enzymatically to remove phosphate, and also subjected to IMAC. This constitutes the control sample for non-specific binding. Bound peptides are collected following selective desorption, and in this case the flow-through fractions may be discarded. The proportional split shown here (⅔ and ⅓) is chosen so that essentially equal amounts of total protein are passed down each IMAC column.

Bound and flow-through fractions are individually reacted with members of a multiplex set of isobaric reagents (A, B, C, D and E; that can be used in any order for labeling and the following description is used for illustration purposes only and is not intended to be limiting in any way) as shown in FIG. 3a. All labeled peptide pools are then combined and treated enzymatically or chemically to remove bound phosphate. The pooled mixture is then analyzed by 1D, 2D or multi-dimensional LC and the peptides are analyzed by MS and subjected to dissociative energy followed by MS/MS analysis of selected ions. Examination of the collected MS/MS collision spectra can now be used to quantify relative peptide abundance and at the same time allow for the specific identification and quantitation of phosphopeptides within the mixture. As an additional measure, the presence or absence of the 'flag' peak C can be used to discriminate between true and non-specific binding to IMAC media (and therefore distinguish true phosphopeptides). If significant amounts of peak C are present in the MS/MS spectrum, the peptide is a non-specific binder, and therefore not a true phosphopeptide.

With this logic applied, the following type of information can be derived from such an experiment (FIG. 3b).

1) True phosphopeptides will exhibit peaks A and/or B. The absence of peaks A and B indicates the peptides were not phosphorylated. The relative intensities of peaks A and B indicate the relative concentration of the phosphorylated form of the peptide in cell lysates 1 and 2, respectively (this statement assumes similar treatments for Samples cell lysates 1 and 2, including similar amounts of samples, or sample fractions, were applied to the IMAC columns).

2) The relative intensities of peaks D and E can be used to determine the relative concentration of any given peptide (and therefore protein) in cell lysates 1 and 2 (all peptides).

3) The relative ratios of peak A to peak D and peak B to peak E can be used to determine the relative stoichiometry of phosphorylation of any given peptide in cell lysates 1 and 2 (e.g. 5%, 10%, 25%; this statement assumes similar treatments for cell lysates 1 and 2, including similar amounts of samples, or sample fractions, were applied to the IMAC columns).

4) The absence or substantial presence of any signal from Peak C can be used to determine whether the peptide was a true or non-specific binder. Absence of peak C indicates that the peptide is a true phosphopeptide. Substantial presence of signal at peak C would indicate that the peptide could bind non-specifically to the IMAC column, and was not a phosphopeptide.

The aforementioned process could be extended to the analysis of additional samples with a larger set of isobaric and/or isomeric labeling reagents. Accordingly, the process could be used for the analysis of three, four, five, six or more different samples (e.g. cell lysates).

Example 4

Figure 6A:
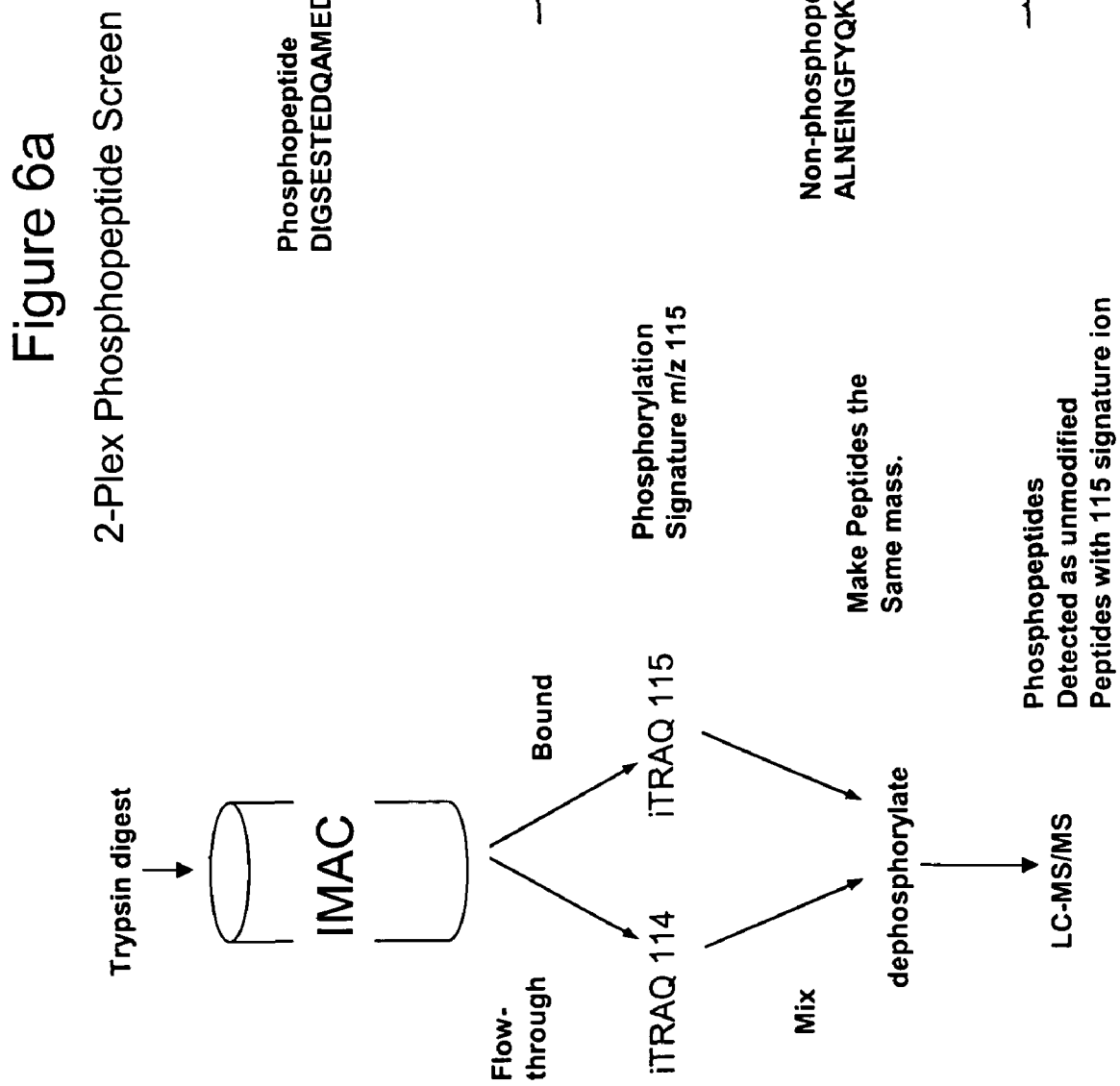
FIG. 6a illustrates a 2-plex-phosphopeptide screen and some associated data.

Analysis Using a Model Phosphoprotein (FIGS. 6a & 6b)

A model phosphoprotein (bovine α-casein) was reduced (TCEP, 37° C.), alkylated (MMTS, 2 hr, Room Temp.) and trypsin digested (1:20 w/w, 37° C., 16 hours).

IMAC conditions: IMAC chromatography was performed using a guard column (5 cm×1 mm) packed with Poros MC resin charged with $Fe^{3+}$ connected to a syringe pump. Samples were loaded in 0.1M acetic acid, and the column washed with 2 ml of 0.1M acetic acid to elute any non-phosphorylated peptides. The bound phosphopeptides were then specifically eluted in 1.5 ml triethylammonium bicarbonate/75% v/v ethanol (pH 8.5).

iTRAQ™ labeling: The collected peptide fractions recovered from the separate bound and flow-through fractions of the IMAC column were then dried and reconstituted in iTRAQ labeling buffer consisting of 75% ethanol/0.25M triethylammonium bicarbonate. 1 mg of each reagent (114 or 115) was added to the respective peptide mixture and allowed to react for 30 min at room temperature. Depending on the workflow used, labeled samples were then treated with alkaline phosphatase (1% w/w, 1 hour, RT) to remove the phosphate groups, and the peptide fractions then combined for LC-MS/MS analysis.

LC-MALDI-MS/MS: Resultant peptide mixtures were separated by capillary RP-HPLC using an LC-Packings Ulti-Mate™ system and spotted with α-cyanohydroxycinnamic acid matrix onto MALDI plates, which were subsequently analyzed on an ABI 4700 Proteomics Analyzer. Peptides were identified from LC-MS/MS data using GPS Explorer™ 2 software. Peak areas of iTRAQ™ reagent signature ions were extracted directly from the mass spectrometer database.

FIGS. 6a and 6b: 2-Plex Phosphopeptide Screen. FIG. 6a illustrates the simplest implementation of this approach. Accordingly, a protein digest mixture can be analyzed for both phospho- and non-phosphopeptides. In this experiment, the presence of phosphate was marked by appearance of a 115 m/z signature ion (bound to the IMAC column), whereas a non-phosphopeptide was coded with a reporter group of m/z 114 (flow through). Although this method does not permit determination of the specific site of phosphorylation, our results have suggested that a greater proportion of phosphorylated peptides can be identified. This is mainly because the phosphate is removed before analysis (which improves MS sensitivity) and isobaric tagging is used to provide a definitive MS/MS signature to indicate the presence or absence of a phosphate group. We compared the phosphopeptides identified in our experiment with other reports for α-casein (FIG. 6b). Most notable is that several of the longer phospho-peptides that are detected more consistently using this methodology.

We claim:

1. A method for analyzing comprising:
   i) selecting more than one sample to be analyzed, wherein the samples each comprise one or more analytes some of which may comprise a modification of interest;
   ii) optionally processing one or more of the samples, or a fraction thereof;
   iii) optionally treating one or more of the samples, or a fraction thereof, with an enzyme or chemical under conditions that remove the modification of interest from analytes so modified, provided that not all of the samples, or fractions thereof, are treated with the enzyme or chemical;
   iv) applying each sample, or a fraction thereof, to an affinity support wherein the affinity support is capable of separating modified from non-modified analytes and all affinity supports comprise the same stationary phase but wherein each sample, or fraction thereof, is applied to a different affinity support;
   v) optionally collecting separately as a fraction the analytes that flow through each affinity support;
   vi) collecting separately as a fraction, after said applying, analytes that bind to each affinity support by eluding the bound analytes under suitable conditions;
   vii) encoding, after said collecting, each fraction of interest containing the one or more analytes that bound to and elute from the affinity support by reaction with a unique isobaric and/or isomeric labeling reagent of a set of isobaric and/or isomeric labeling reagents;
   viii) optionally encoding each fraction of interest containing the one or more analytes that flowed through the affinity support by reaction with a unique isobaric and/or isomeric labeling reagent of the set of isobaric and/or isomeric labeling reagents;
   ix) mixing, after said encoding, two or more fractions encoded with isobaric and/or isomeric labeling reagents, providing a mixture thereof;
   x) optionally adding a known amount of one or more calibration standards to the mixture;
   xi) treating the mixture with ma enzyme or chemical under conditions that remove the modification of interest from analytes so modified;
   xii) optionally separating the mixture; and
   xiii) analyzing the mixture, or one or more fractions thereof, by mass spectrometer to thereby obtain daughter ion fragments for one or more analytes of the mixture mid signature ions associated with each unique labeling reagent.

2. The method of claim 1, further comprising:
   a) determining whether or not analytes comprising the modification specifically interact with the affinity support.

3. The method of claim 1, further comprising:
   a) identifying one or more of the analytes in the mixture by analysis of daughter ion fragments; and/or
   b) determining the relative and/or absolute amount of a particular modified analyte and its corresponding unmodified analyte in each of the samples.

4. The method of claim 3, further comprising;
   a) repeating steps a) and b) one or more times to thereby determine, for a different analyte, the relative and/or absolute amount of a particular modified analyte and its corresponding unmodified analyte in each of the samples.

5. The method of claim 1, wherein two or more samples, each comprising one or more proteins and/or phosphoproteins as analytes, are selected.

6. The method of claim 5, wherein each sample is processed by treatment with trypsin to thereby digest the proteins and/or phosphoproteins into peptides and/or phosphopeptides.

7. The method of claim 6, wherein each processed sample is applied to an affinity support that can separate phosphopeptides from unmodified peptides.

8. The method of claim 7, wherein a fraction comprising analytes that bind to each affinity support is collected and the fraction obtained from each different column is encoded with a unique labeling reagent from the set of isomeric and/or isobaric labeling reagents.

9. The method of claim 8, wherein a fraction comprising analytes that flowed through each of affinity supports is collected and the fraction obtained from each different column is encoded with a unique labeling reagent from the set of isomeric and/or isobaric labeling reagents.

10. The method of claim 9, wherein the encoded fractions are mixed to form a mixture and the mixture is treated with one or more phosphatase enzymes to thereby dephosphorylate the phosphopeptides.

11. The method of claim 10, further comprising:
    a) identifying one or more of the peptides in the mixture by analysis of daughter ion fragments; and/or
    b) determining the relative and/or absolute amount of a particular phosphopeptide and its corresponding unmodified peptide in each of two or more of the samples.

12. The method of claim 11, further comprising;
    a) repeating steps a) and b) one or more times to thereby determine, for a different peptide, the identity and/or the relative and/or absolute amount of a particular phosphopeptide and its corresponding unmodified peptide in each of two or more of the samples.

13. The method of claim 1, wherein a first sample and a second sample is selected, each sample comprising one or more proteins and/or phosphoproteins as analytes.

14. The method of claim 13, wherein the first sample and the second sample are each processed by treatment with trypsin to thereby digest the proteins and/or phosphoproteins into peptides and/or phosphopeptides.

15. The method of claim 14, wherein a fraction of each processed sample is mixed to form a specificity control mixture.

16. The method of claim 15, wherein the specificity control mixture is treated with one or more phosphatase enzymes to thereby dephosphorylate the phosphopeptides.

17. The method of claim 16, wherein each fraction is applied to an affinity support that can separate phosphopeptides from unmodified peptides, wherein the fractions are:
    a) all or part of the remainder of the first sample;
    b) all or part of the remainder of the second sample; and
    c) all or part of the specificity control mixture.

18. The method of claim 17, wherein fractions comprising analytes that bind to each affinity support are collected and each fraction obtained from each different column is encoded with a unique labeling reagent from the set of isomeric and/or isobaric labeling reagents.

19. The method of claim 18, wherein fractions comprising analytes that flowed through each affinity support are collected and at least the flow through fractions obtained from the first sample and the second sample are encoded with a unique labeling reagent from the set of isomeric and/or isobaric labeling reagents.

20. The method of claim 19, wherein the encoded fractions are mixed to form a mixture and the mixture is treated with one or more phosphatase enzymes to thereby dephosphorylate the phosphopeptides.

21. The method of claim 20, further comprising determining whether or not one or more of the peptides comprising the phosphate modification specifically interact with the affinity support.

22. The method of claim 21, further comprising:
a) identifying one or more of the peptides in the mixture by analysis of daughter ion fragments; and/or
b) determining the relative and/or absolute amount of the identified peptide and its corresponding phosphopeptide in each of the first sample and the second sample.

23. The method of claim 22, further comprising;
a) repeating steps a) and b) one or more times to thereby determine, for a different peptide, the relative and/or absolute amount of a particular phosphopeptide and its corresponding unmodified peptide in the first sample and the second sample.

24. The method of claim 22, further comprising determining the relative and/or absolute amount of the protein and phosphoprotein associated with the identified peptide and associated phosphopeptide, respectively, in each of the first sample and the second sample.

25. The method of claim 24, wherein each of the first sample and the second sample is a cell lysate.

26. The method of claim 1, wherein the analyte or analytes are nucleic acids, carbohydrates, lipids, steroids or other small molecules of molecular weight of less than 1500 daltons.

* * * * *